US005932465A

United States Patent [19]
Loughney

[11] Patent Number: 5,932,465
[45] Date of Patent: Aug. 3, 1999

[54] PHOSPHODIESTERASE 8A

[75] Inventor: Kate Loughney, Seattle, Wash.

[73] Assignee: ICOS Corporation, Bothell, Wash.

[21] Appl. No.: 08/951,648

[22] Filed: Oct. 16, 1997

[51] Int. Cl.$^6$ .............................. C12N 9/16; C12N 15/55; C12N 15/63

[52] U.S. Cl. ................. 435/196; 435/252.3; 435/254.11; 435/325; 435/320.1; 536/23.2

[58] Field of Search ..................................... 435/196, 199, 435/325, 252.3, 254.11; 536/23.2

[56] References Cited

FOREIGN PATENT DOCUMENTS

WO 91/09955  7/1991  WIPO .
WO 92/20808  11/1992  WIPO .
WO 94/12650  6/1994  WIPO .

OTHER PUBLICATIONS

Fisher, D.A. et al. *Biochem. Biophys. Res. Comm.* 246:570–577 (1998).

Lee, N.H. et al. *PNAS* 92:8303–8307 (1995).

Ausbel, et al. (Eds.), "Screening of Recombinant DNA Libraries," *Protocols in Molecular Biology*, John Wiley & Sons (1994), pp. 6.0.3–6.4.10.

Beavo, "Cyclic Nucleotide Phosphodiesterases: Functional Implications of Multiple Isoforms," *Physiol.Rev.* 75:725–748 (1995).

Bolger, et al., "A Family of Human Phosphodiesterases Homologous to the dunce Learning and Memory Gene Product of *Drosophila melanogaster* Are Potential Targets for Antidepressant Drugs," *Mol.Cell.Biol.* 13:6558–6571 (1993).

Capecchi, "Altering the Genome by Homologous Recombination," *Science* 244:1288–1292 (1989).

Charbonneau, "Structure–Function Relationships Among Cyclic Nucleotide Phosphodiesterases," *Mol.Pharmacol. Cell.Regul.* 2:267–298 (1990).

Charbonneau, et al., "Identification of a conserved domain among cyclic nucleotide phosphodiesterases from diverse species," *Proc.Nat'l.Acad.Sci.(USA)* 83:9308–9312 (1986).

Chumakov, et al., "A YAC cotig map of the human genome," *Nature* 377(Supp):175–297 (1995).

Collins, et al., "The Human B–Subunit of Rod Photoreceptor cGMP Phosphodiesterase: Complete Retinal cDNA Sequence and Evidence for Expression in Brain," *Genomics* 13:698–704 (1992).

Cooke, et al., "Allele Loss on Chromosome Arm 6q and Fine Mapping of the Region at 6q27 in Epithelial Ovarian Cancer," *Genes, Chromosomes & Cancer*, 15:223–233 (1996).

Davies, et al., "A genome–wide search for human type 1 diabetes susceptibility genes," *Nature* 371:130–136 (1994).

Francis, et al., "Zinc Interactions and Conserved Motifs of the cGMP–binding cGMP–specific Phosphodiesterase Suggest That It Is a Zinc Hydrolase*," *J.Biol.Chem.* 269:22477–22480 (1994).

Hoffman and Winston, "A ten–minute DNA preparation from yeast efficiently releases autonomous plasmids for transformation of *Escherichia coli*," *Gene*, 57:267–272 (1987).

Liang, et al., "Evidence of allelic imbalance of chromosome 6 in human astrocytomas," *Neurology* 44:533–536 (1994).

Loughney, et al., "Isolation and Characterization of cDNAs Corresponding to Two Human Calcium , Calmodulin–regulated, 3' ,5'–Cyclic Nucleotide Phosphodiesterases*," *J.Biol.Chem.* 271:796–806 (1996).

Loughney and Ferguson, in Phosphodiesterase Inhibitors, Schudt, et al. (Eds.), "Identification and Quantification of PDE Isoenzymes and Subtypes by Molecular Biological Methods," Academic Press:New York, New York (1996) pp. 1–19.

Luo, et al., "Affected–Sib–Pair Mapping of a Novel Susceptibility Gene to Insulin–Dependent Diabetes Mellitus (IDDM8) on Chromosome 6q25–q27," *Am.J.Hum.Genet.* 57:911–919 (1995d).

Manganiello, et al., "Diversity in Cyclic Nucleotide Phosphodiesterase Isoenzyme Families," *Arch.Biochem.Acta.* 322:1–13 (1995).

Matsumie, et al., "Localization of a Gene for an Autosomal Recessive Form of Juvenile Parkinsonism to Chromosome 6q25.2–27," *Am.J.Hum.Genet.* 60:588–596 (1997).

McAllister–Lucas, et al,. "The Structure of a Bovine Lung cGMP–binding, cGMP–specific Phosphodiesterase Deduced from a cDNA Clone*," *J.Biol.Chem.* 268:22863–22873 (1993).

McAllister–Lucas, et al., "An Essential Aspartic Acid at Each of Two Allosteric cGMP–binding Sites of a cGMP–specific Phosphodiesterase*," *J.Biol.Chem.* 270:1–9 (1995).

Meacci, et al., "Molecular cloning and expression of human myocardial cGMP–inhibited cAMP phosphodiesterase," *Proc.Natl.Acad.Sci.(USA)* 89:3721–3725 (1992).

Michaeli, et al., "Isolation and Characterization of a Previously Undetected Human cAMP Phosphodiesterase by Complementation of cAMP Phosphodiesterase–deficient *Saccharomyces cerevisiae*,*" *J.Biol.Chem.* 17:12925–12932 (1993).

Miki, et al., "Characterization of the cDNA and Gene Encoding Human PDE3B, the cGIP1 Isoform of the Human Cyclic GMP–Inhibited Cyclic Nucleotide Phosphodiesterase Family," *Genomics* 36:476–485 (1996).

Parasa, et al., "Cytogenetic and Molecular Analysis of 6q Deletions in Burkitt's Lymphoma Cell Lines," *Genes, Chdromosomes & Cancer*, 9:13–18 (1994).

(List continued on next page.)

Primary Examiner—Dian C. Jacobson
Attorney, Agent, or Firm—Marshall, O'Toole, Gerstein, Murray & Borun

[57] ABSTRACT

The present invention provides novel human PDE8 polypeptides, polynucleotides encoding the polypeptides, expression constructs comprising the polynucleotides, host cells transformed with the expression constructs; methods for producing PDE8 polypeptides; antisense polynucleotides; and antibodies specifically immunoreactive with the PDE8 polypeptides.

14 Claims, No Drawings

OTHER PUBLICATIONS

Pittler, et al., "Molecular Characterization of Human and Bovine Rod Photoreceptor cGMP Phosphodiesterase α–Subunit and Chromosomal Localization of the Human Gene," *Genomics* 6:272–283 (1990).

Piriev, et al., "Gene Structure and Amino Acid Sequence of the Human Cone Photoreceptor cGMP–Phosphodiesterase α' Subunit (PDEA2) and Its Chromosomal Localization to 10q24," *Genomics* 28:429–435 (1995).

Price, et al., "Expression of Heterologous Proteins in *Saccharomyces cerevisiae* Using the ADH2 Promoter," *Meth.Enzymol.* 185:308–315 (1990).

Queimado, et al., "Identification of Two Distinct Regions of Deletion at 6q in Gastric Carcinoma," *Genes, Chromosomes & Cancer* 14:28–34 (1995).

Rosman, et al., "Isolation and characterization of human cDNAs encoding a cGMP–stimulated 3', 5'–cyclic nucleotide phosphodiesterase[1]," *Gene* 191:89–95 (1997).

Saito, et al., "Definition of a Commonly Deleted Region in Ovarian Cancers to a 300–kb Segment of Chromosome 6q27[1]," *Cancer Res.* 56:5586–5589 (1996).

Sambrook, et al. (Eds.), Molecular Cloning: A Laboratory Manual, Cold Spring Harbor Laboratory Press:Cold Spring Harbor, New York (1989), pp. 9.47–9.51.

Tahara, et al., "Genomic Localization of Novel Candidate Tumor Suppressor Gene Loci in Human Parathyroid Adenomas[1]," *Cancer Res.* 56:599–605 (1996).

Weinberg, "Tumor Suppressor Genes," *Science* 254:1138–1146 (1991).

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
      (A) LENGTH: 2298 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..2298
      (D) OTHER INFORMATION:
         /note= "The amino acid encoded by nucleotides 868-870 is
         either Pro or Lys."

(xi) SEQUENCE DESCRIPTION: SEQ ID NO:1:

```
TTG ACA GAT GAA AAA GTG AAG GCA TAT CTT TCT CTT CAC CCC CAG GTA        48
Leu Thr Asp Glu Lys Val Lys Ala Tyr Leu Ser Leu His Pro Gln Val
 1               5                  10                  15

TTA GAT GAA TTT GTA TCT GAA AGT GTT AGT GCA GAG ACA GTA GAG AAA        96
Leu Asp Glu Phe Val Ser Glu Ser Val Ser Ala Glu Thr Val Glu Lys
            20                  25                  30

TGG CTG AAG AGG AAG AAC AAC AAA TCA GAA GAT GAA TCG GCT CCT AAG       144
Trp Leu Lys Arg Lys Asn Asn Lys Ser Glu Asp Glu Ser Ala Pro Lys
        35                  40                  45

GAA GTC AGC AGG TAC CAA GAT ACG AAT ATG CAG GGA GTT GTA TAT GAA       192
Glu Val Ser Arg Tyr Gln Asp Thr Asn Met Gln Gly Val Val Tyr Glu
    50                  55                  60

CTA AAC AGC TAT ATA GAA CAA CGG TTG GAC ACA GGA GGA GAC AAC CAG       240
Leu Asn Ser Tyr Ile Glu Gln Arg Leu Asp Thr Gly Gly Asp Asn Gln
65                  70                  75                  80

CTA CTC CTC TAT GAA CTG AGC AGC ATC ATT AAA ATA GCC ACA AAA GCC       288
Leu Leu Leu Tyr Glu Leu Ser Ser Ile Ile Lys Ile Ala Thr Lys Ala
                85                  90                  95

GAT GGA TTT GCA CTG TAT TTC CTT GGA GAG TGC AAT AAT AGC CTG TGT       336
Asp Gly Phe Ala Leu Tyr Phe Leu Gly Glu Cys Asn Asn Ser Leu Cys
            100                 105                 110

ATA TTC ACG CCA CCT GGG ATA AAG GAA GGA AAA CCC CGC CTC ATC CCT       384
Ile Phe Thr Pro Pro Gly Ile Lys Glu Gly Lys Pro Arg Leu Ile Pro
        115                 120                 125

GCT GGG CCC ATC ACT CAG GGC ACC ACC GTC TCT GCT TAT GTG GCC AAG       432
Ala Gly Pro Ile Thr Gln Gly Thr Thr Val Ser Ala Tyr Val Ala Lys
    130                 135                 140
```

```
TCC AGG AAA ACA CTG CTA GTA GAA GAC ATC CTT GGA GAT GAA CGA TTT      480
Ser Arg Lys Thr Leu Leu Val Glu Asp Ile Leu Gly Asp Glu Arg Phe
145                 150                 155                 160

CCA AGA GGT ACT GGA CTG GAA TCA GGG ACT CGT ATC CAG TCT GTT CTT      528
Pro Arg Gly Thr Gly Leu Glu Ser Gly Thr Arg Ile Gln Ser Val Leu
            165                 170                 175

TGC TTA CCA ATT GTC ACT GCA ATT GGT GAC TTG ATT GGT ATT CTC GAG      576
Cys Leu Pro Ile Val Thr Ala Ile Gly Asp Leu Ile Gly Ile Leu Glu
        180                 185                 190

CTG TAT CGG CAC TGG GGC AAA GAA GCC TTC TGT CTT AGT CAC CAG GAG      624
Leu Tyr Arg His Trp Gly Lys Glu Ala Phe Cys Leu Ser His Gln Glu
    195                 200                 205

GTT GCA ACA GCA AAT CTT GCC TGG GCT TCA GTA GCA ATA CAT CAG GTG      672
Val Ala Thr Ala Asn Leu Ala Trp Ala Ser Val Ala Ile His Gln Val
210                 215                 220

CAG GTA TGC AGA GGC CTT GCC AAA CAG ACA GAA TTG AAT GAC TTC CTA      720
Gln Val Cys Arg Gly Leu Ala Lys Gln Thr Glu Leu Asn Asp Phe Leu
225                 230                 235                 240

CTC GAC GTA TCA AAA ACA TAT TTT GAT AAC ATA GTT GCA ATA GAT TCT      768
Leu Asp Val Ser Lys Thr Tyr Phe Asp Asn Ile Val Ala Ile Asp Ser
            245                 250                 255

CTA CTT GAA CAC ATA ATG ATA TAT GCA AAA AAC CTG GTG AAT GCC GAT      816
Leu Leu Glu His Ile Met Ile Tyr Ala Lys Asn Leu Val Asn Ala Asp
        260                 265                 270

CGT TGT GCA CTT TTC CAG GTG GAC CAT AAG AAC AAG GAG TTA TAT TCA      864
Arg Cys Ala Leu Phe Gln Val Asp His Lys Asn Lys Glu Leu Tyr Ser
    275                 280                 285

GAC CYT TTT GAT ATT GGA GAG GAA AAG GAA GGA AAA CCT GTC TTC AAG      912
Asp Xaa Phe Asp Ile Gly Glu Glu Lys Glu Gly Lys Pro Val Phe Lys
290                 295                 300

AAG ACC AAA GAG ATA AGA TTT TCA ATT GAG AAA GGA ATT GCT GGC CAA      960
Lys Thr Lys Glu Ile Arg Phe Ser Ile Glu Lys Gly Ile Ala Gly Gln
305                 310                 315                 320

GTA GCA AGA ACA GGG GAA GTC CTG AAC ATT CCA GAT GCC TAT GCA GAC     1008
Val Ala Arg Thr Gly Glu Val Leu Asn Ile Pro Asp Ala Tyr Ala Asp
            325                 330                 335

CCA CGC TTT AAC AGA GAA GTA GAC TTG TAC ACA GGC TAC ACC ACG CGG     1056
Pro Arg Phe Asn Arg Glu Val Asp Leu Tyr Thr Gly Tyr Thr Thr Arg
        340                 345                 350

AAC ATC CTG TGC ATG CCC ATC GTC AGC CGA GGC AGC GTG ATA GGT GTG     1104
Asn Ile Leu Cys Met Pro Ile Val Ser Arg Gly Ser Val Ile Gly Val
    355                 360                 365

GTG CAG ATG GTC AAC AAA ATC AGT GGC AGT GCC TTC TCT AAA ACA GAT     1152
Val Gln Met Val Asn Lys Ile Ser Gly Ser Ala Phe Ser Lys Thr Asp
370                 375                 380

GAA AAC AAC TTC AAA ATG TTT GCC GTC TTT TGT GCT TTA GCC TTA CAC     1200
Glu Asn Asn Phe Lys Met Phe Ala Val Phe Cys Ala Leu Ala Leu His
385                 390                 395                 400

TGT GCT AAT ATG TAT CAT AGA ATT CGC CAC TCA GAG TGC ATT TAC CGG     1248
Cys Ala Asn Met Tyr His Arg Ile Arg His Ser Glu Cys Ile Tyr Arg
            405                 410                 415

GTA ACG ATG GAA AAG CTG TCC TAC CAT AGC ATT TGT ACT TCA GAA GAG     1296
Val Thr Met Glu Lys Leu Ser Tyr His Ser Ile Cys Thr Ser Glu Glu
        420                 425                 430

TGG CAA GGT CTC ATG CAA TTC ACC CTT CCC GTG CGT CTC TGC AAA GAA     1344
Trp Gln Gly Leu Met Gln Phe Thr Leu Pro Val Arg Leu Cys Lys Glu
    435                 440                 445

ATT GAA TTA TTC CAC TTT GAC ATT GGT CCT TTT GAA AAC ATG TGG CCT     1392
Ile Glu Leu Phe His Phe Asp Ile Gly Pro Phe Glu Asn Met Trp Pro
450                 455                 460
```

| | |
|---|---|
| GGA ATT TTT GTC TAC ATG GTT CAT CGG TCC TGT GGG ACA TCC TGC TTT<br>Gly Ile Phe Val Tyr Met Val His Arg Ser Cys Gly Thr Ser Cys Phe<br>465                          470                        475                      480 | 1440 |
| GAG CTT GAA AAG TTG TGT CGT TTT ATT ATG TCT GTG AAG AAG AAC TAT<br>Glu Leu Glu Lys Leu Cys Arg Phe Ile Met Ser Val Lys Lys Asn Tyr<br>                         485                        490                      495 | 1488 |
| CGG CGG GTT CCT TAT CAC AAC TGG AAG CAT GCG GTC ACT GTA GCA CAC<br>Arg Arg Val Pro Tyr His Asn Trp Lys His Ala Val Thr Val Ala His<br>                   500                        505                      510 | 1536 |
| TGC ATG TAT GCC ATA CTT CAG AAC AAT CAC ACG CTT TTC ACA GAC CTT<br>Cys Met Tyr Ala Ile Leu Gln Asn Asn His Thr Leu Phe Thr Asp Leu<br>                 515                        520                      525 | 1584 |
| GAG CGC AAA GGA CTG CTG ATT GCG TGT CTG TGT CAT GAC CTG GAC CAC<br>Glu Arg Lys Gly Leu Leu Ile Ala Cys Leu Cys His Asp Leu Asp His<br>530                          535                        540 | 1632 |
| AGG GGC TTC AGT AAC AGC TAC CTG CAG AAG TTC GAC CAC CCT CTG GCC<br>Arg Gly Phe Ser Asn Ser Tyr Leu Gln Lys Phe Asp His Pro Leu Ala<br>545                          550                        555                      560 | 1680 |
| GCT CTC TAC TCC ACT TCC ACC ATG GAG CAG CAC CAC TTC TCC CAG ACT<br>Ala Leu Tyr Ser Thr Ser Thr Met Glu Gln His His Phe Ser Gln Thr<br>                   565                        570                      575 | 1728 |
| GTG TCC ATC CTC CAG TTG GAA GGG CAC AAT ATC TTC TCC ACT CTG AGC<br>Val Ser Ile Leu Gln Leu Glu Gly His Asn Ile Phe Ser Thr Leu Ser<br>                 580                        585                      590 | 1776 |
| TCC AGT GAA TAT GAG CAG GTG CTT GAG ATC ATC CGC AAA GCA ATC ATT<br>Ser Ser Glu Tyr Glu Gln Val Leu Glu Ile Ile Arg Lys Ala Ile Ile<br>             595                        600                      605 | 1824 |
| GCC ACA GAC CTT GCT TTA TAC TTT GGA AAC AGG AAG CAG TTG GAA GAG<br>Ala Thr Asp Leu Ala Leu Tyr Phe Gly Asn Arg Lys Gln Leu Glu Glu<br>610                          615                        620 | 1872 |
| ATG TAC CAG ACC GGA TCA CTA AAC CTT AAT AAT CAA TCA CAT AGA GAC<br>Met Tyr Gln Thr Gly Ser Leu Asn Leu Asn Asn Gln Ser His Arg Asp<br>625                          630                        635                      640 | 1920 |
| CGT GTA ATT GGT TTG ATG ATG ACT GCC TGT GAC CTT TGT TCT GTG ACA<br>Arg Val Ile Gly Leu Met Met Thr Ala Cys Asp Leu Cys Ser Val Thr<br>                 645                        650                      655 | 1968 |
| AAA CTG TGG CCC GTT ACA AAA TTG ACG GCA AAT GAT ATA TAT GCA GAA<br>Lys Leu Trp Pro Val Thr Lys Leu Thr Ala Asn Asp Ile Tyr Ala Glu<br>             660                        665                      670 | 2016 |
| TTC TGG GCT GAG GGT GAT GAA ATG AAG AAA TTG GGA ATA CAG CCT ATT<br>Phe Trp Ala Glu Gly Asp Glu Met Lys Lys Leu Gly Ile Gln Pro Ile<br>             675                        680                      685 | 2064 |
| CCT ATG ATG GAC AGA GAC AAG AAG GAT GAA GTC CCC CAA GGC CAG CTT<br>Pro Met Met Asp Arg Asp Lys Lys Asp Glu Val Pro Gln Gly Gln Leu<br>             690                        695                      700 | 2112 |
| GGG TTC TAC AAT GCC GTG GCC ATT CCC TGC TAT ACA ACC CTT ACC CAG<br>Gly Phe Tyr Asn Ala Val Ala Ile Pro Cys Tyr Thr Thr Leu Thr Gln<br>705                          710                        715                      720 | 2160 |
| ATC CTC CCT CCC ACG GAG CCT CTT CTG AAA GCA TGC AGG GAT AAT CTC<br>Ile Leu Pro Pro Thr Glu Pro Leu Leu Lys Ala Cys Arg Asp Asn Leu<br>                 725                        730                      735 | 2208 |
| AGT CAG TGG GAG AAG GTG ATT CGA GGG GAG GAG ACT GCA ACC TGG ATT<br>Ser Gln Trp Glu Lys Val Ile Arg Gly Glu Glu Thr Ala Thr Trp Ile<br>             740                        745                      750 | 2256 |
| TCA TCC CCA TCC GTG GCT CAG AAG GCA GCT GCA TCT GAA GAT<br>Ser Ser Pro Ser Val Ala Gln Lys Ala Ala Ala Ser Glu Asp<br>             755                        760                      765 | 2298 |

(2) INFORMATION FOR SEQ ID NO:2:

(i) SEQUENCE CHARACTERISTICS:
        (A) LENGTH: 766 amino acids
        (B) TYPE: amino acid
        (D) TOPOLOGY: linear (ii) MOLECULE TYPE: protein (ix) FEATURE:
        (D) OTHER INFORMATION:
            /note= "The amino acid at position 290 is either Pro
            or Leu."

(xi) SEQUENCE DESCRIPTION: SEQ ID NO:2:

```
Leu Thr Asp Glu Lys Val Lys Ala Tyr Leu Ser Leu His Pro Gln Val
 1               5                  10                  15

Leu Asp Glu Phe Val Ser Glu Ser Val Ser Ala Glu Thr Val Glu Lys
                20                  25                  30

Trp Leu Lys Arg Lys Asn Asn Lys Ser Glu Asp Glu Ser Ala Pro Lys
             35                  40                  45

Glu Val Ser Arg Tyr Gln Asp Thr Asn Met Gln Gly Val Val Tyr Glu
         50                  55                  60

Leu Asn Ser Tyr Ile Glu Gln Arg Leu Asp Thr Gly Gly Asp Asn Gln
 65                  70                  75                  80

Leu Leu Leu Tyr Glu Leu Ser Ser Ile Ile Lys Ile Ala Thr Lys Ala
                 85                  90                  95

Asp Gly Phe Ala Leu Tyr Phe Leu Gly Glu Cys Asn Asn Ser Leu Cys
            100                 105                 110

Ile Phe Thr Pro Pro Gly Ile Lys Glu Gly Lys Pro Arg Leu Ile Pro
        115                 120                 125

Ala Gly Pro Ile Thr Gln Gly Thr Val Ser Ala Tyr Val Ala Lys
    130                 135                 140

Ser Arg Lys Thr Leu Leu Val Glu Asp Ile Leu Gly Asp Glu Arg Phe
145                 150                 155                 160

Pro Arg Gly Thr Gly Leu Glu Ser Gly Thr Arg Ile Gln Ser Val Leu
                165                 170                 175

Cys Leu Pro Ile Val Thr Ala Ile Gly Asp Leu Ile Gly Ile Leu Glu
            180                 185                 190

Leu Tyr Arg His Trp Gly Lys Glu Ala Phe Cys Leu Ser His Gln Glu
        195                 200                 205

Val Ala Thr Ala Asn Leu Ala Trp Ala Ser Val Ala Ile His Gln Val
    210                 215                 220

Gln Val Cys Arg Gly Leu Ala Lys Gln Thr Glu Leu Asn Asp Phe Leu
225                 230                 235                 240

Leu Asp Val Ser Lys Thr Tyr Phe Asp Asn Ile Val Ala Ile Asp Ser
                245                 250                 255

Leu Leu Glu His Ile Met Ile Tyr Ala Lys Asn Leu Val Asn Ala Asp
            260                 265                 270

Arg Cys Ala Leu Phe Gln Val Asp His Lys Asn Lys Glu Leu Tyr Ser
        275                 280                 285

Asp Xaa Phe Asp Ile Gly Glu Glu Lys Glu Gly Lys Pro Val Phe Lys
    290                 295                 300

Lys Thr Lys Glu Ile Arg Phe Ser Ile Glu Lys Gly Ile Ala Gly Gln
305                 310                 315                 320

Val Ala Arg Thr Gly Glu Val Leu Asn Ile Pro Asp Ala Tyr Ala Asp
                325                 330                 335
```

-continued

Pro Arg Phe Asn Arg Glu Val Asp Leu Tyr Thr Gly Tyr Thr Thr Arg
            340                 345                 350

Asn Ile Leu Cys Met Pro Ile Val Ser Arg Gly Ser Val Ile Gly Val
            355                 360                 365

Val Gln Met Val Asn Lys Ile Ser Gly Ser Ala Phe Ser Lys Thr Asp
370                 375                 380

Glu Asn Asn Phe Lys Met Phe Ala Val Phe Cys Ala Leu Ala Leu His
385                 390                 395                 400

Cys Ala Asn Met Tyr His Arg Ile Arg His Ser Glu Cys Ile Tyr Arg
                405                 410                 415

Val Thr Met Glu Lys Leu Ser Tyr His Ser Ile Cys Thr Ser Glu Glu
            420                 425                 430

Trp Gln Gly Leu Met Gln Phe Thr Leu Pro Val Arg Leu Cys Lys Glu
            435                 440                 445

Ile Glu Leu Phe His Phe Asp Ile Gly Pro Phe Glu Asn Met Trp Pro
450                 455                 460

Gly Ile Phe Val Tyr Met Val His Arg Ser Cys Gly Thr Ser Cys Phe
465                 470                 475                 480

Glu Leu Glu Lys Leu Cys Arg Phe Ile Met Ser Val Lys Lys Asn Tyr
                485                 490                 495

Arg Arg Val Pro Tyr His Asn Trp Lys His Ala Val Thr Val Ala His
            500                 505                 510

Cys Met Tyr Ala Ile Leu Gln Asn Asn His Thr Leu Phe Thr Asp Leu
            515                 520                 525

Glu Arg Lys Gly Leu Leu Ile Ala Cys Leu Cys His Asp Leu Asp His
530                 535                 540

Arg Gly Phe Ser Asn Ser Tyr Leu Gln Lys Phe Asp His Pro Leu Ala
545                 550                 555                 560

Ala Leu Tyr Ser Thr Ser Thr Met Glu Gln His His Phe Ser Gln Thr
                565                 570                 575

Val Ser Ile Leu Gln Leu Glu Gly His Asn Ile Phe Ser Thr Leu Ser
            580                 585                 590

Ser Ser Glu Tyr Glu Gln Val Leu Glu Ile Ile Arg Lys Ala Ile Ile
            595                 600                 605

Ala Thr Asp Leu Ala Leu Tyr Phe Gly Asn Arg Lys Gln Leu Glu Glu
610                 615                 620

Met Tyr Gln Thr Gly Ser Leu Asn Leu Asn Asn Gln Ser His Arg Asp
625                 630                 635                 640

Arg Val Ile Gly Leu Met Met Thr Ala Cys Asp Leu Cys Ser Val Thr
                645                 650                 655

Lys Leu Trp Pro Val Thr Lys Leu Thr Ala Asn Asp Ile Tyr Ala Glu
            660                 665                 670

Phe Trp Ala Glu Gly Asp Glu Met Lys Lys Leu Gly Ile Gln Pro Ile
            675                 680                 685

Pro Met Met Asp Arg Asp Lys Lys Asp Glu Val Pro Gln Gly Gln Leu
690                 695                 700

Gly Phe Tyr Asn Ala Val Ala Ile Pro Cys Tyr Thr Thr Leu Thr Gln
705                 710                 715                 720

Ile Leu Pro Pro Thr Glu Pro Leu Leu Lys Ala Cys Arg Asp Asn Leu
                725                 730                 735

Ser Gln Trp Glu Lys Val Ile Arg Gly Glu Glu Thr Ala Thr Trp Ile
            740                 745                 750

Ser Ser Pro Ser Val Ala Gln Lys Ala Ala Ala Ser Glu Asp
            755                 760                 765

(2) INFORMATION FOR SEQ ID NO:3:

(i) SEQUENCE CHARACTERISTICS:
        (A) LENGTH: 4389 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..2411

(xi) SEQUENCE DESCRIPTION: SEQ ID NO:3:

```
GC TTC GCC CTC GCC GCC GCG GCC GCG CTG CTC TTC GGC TCC GAC ATG         47
   Phe Ala Leu Ala Ala Ala Ala Ala Leu Leu Phe Gly Ser Asp Met
   1               5                  10                  15

GAA GAT GGA CCT TCT AAT AAT GCG AGC TGC TTC CGA AGG CTG ACC GAG        95
Glu Asp Gly Pro Ser Asn Asn Ala Ser Cys Phe Arg Arg Leu Thr Glu
                20                  25                  30

TGC TTC CTG AGC CCC AGT TTG ACA GAT GAA AAA GTG AAG GCA TAT CTT       143
Cys Phe Leu Ser Pro Ser Leu Thr Asp Glu Lys Val Lys Ala Tyr Leu
            35                  40                  45

TCT CTT CAC CCC CAG GTA TTA GAT GAA TTT GTA TCT GAA AGT GTT AGT       191
Ser Leu His Pro Gln Val Leu Asp Glu Phe Val Ser Glu Ser Val Ser
        50                  55                  60

GCA GAG ACA GTA GAG AAA TGG CTG AAG AGG AAG AAC AAC AAA TCA GAA       239
Ala Glu Thr Val Glu Lys Trp Leu Lys Arg Lys Asn Asn Lys Ser Glu
65                  70                  75

GAT GAA TCG GCT CCT AAG GAA GTC AGC AGG TAC CAA GAT ACG AAT ATG       287
Asp Glu Ser Ala Pro Lys Glu Val Ser Arg Tyr Gln Asp Thr Asn Met
 80                  85                  90                  95

CAG GGA GTT GTA TAT GAA CTA AAC AGC TAT ATA GAA CAA CGG TTG GAC       335
Gln Gly Val Val Tyr Glu Leu Asn Ser Tyr Ile Glu Gln Arg Leu Asp
                100                 105                 110

ACA GGA GGA GAC AAC CAG CTA CTC CTC TAT GAA CTG AGC AGC ATC ATT       383
Thr Gly Gly Asp Asn Gln Leu Leu Leu Tyr Glu Leu Ser Ser Ile Ile
            115                 120                 125

AAA ATA GCC ACA AAA GCC GAT GGA TTT GCA CTG TAT TTC CTT GGA GAG       431
Lys Ile Ala Thr Lys Ala Asp Gly Phe Ala Leu Tyr Phe Leu Gly Glu
        130                 135                 140

TGC AAT AAT AGC CTG TGT ATA TTC ACG CCA CCT GGG ATA AAG GAA GGA       479
Cys Asn Asn Ser Leu Cys Ile Phe Thr Pro Pro Gly Ile Lys Glu Gly
145                 150                 155

AAA CCC CGC CTC ATC CCT GCT GGG CCC ATC ACT CAG GGC ACC ACC GTC       527
Lys Pro Arg Leu Ile Pro Ala Gly Pro Ile Thr Gln Gly Thr Thr Val
160                 165                 170                 175

TCT GCT TAT GTG GCC AAG TCC AGG AAA ACA CTG CTA GTA GAA GAC ATC       575
Ser Ala Tyr Val Ala Lys Ser Arg Lys Thr Leu Leu Val Glu Asp Ile
                180                 185                 190

CTT GGA GAT GAA CGA TTT CCA AGA GGT ACT GGA CTG GAA TCA GGG ACT       623
Leu Gly Asp Glu Arg Phe Pro Arg Gly Thr Gly Leu Glu Ser Gly Thr
            195                 200                 205

CGT ATC CAG TCT GTT CTT TGC TTA CCA ATT GTC ACT GCA ATT GGT GAC       671
Arg Ile Gln Ser Val Leu Cys Leu Pro Ile Val Thr Ala Ile Gly Asp
        210                 215                 220

TTG ATT GGT ATT CTC GAG CTG TAT CGG CAC TGG GGC AAA GAA GCC TTC       719
Leu Ile Gly Ile Leu Glu Leu Tyr Arg His Trp Gly Lys Glu Ala Phe
225                 230                 235
```

| | | |
|---|---|---|
| TGT CTT AGT CAC CAG GAG GTT GCA ACA GCA AAT CTT GCC TGG GCT TCA<br>Cys Leu Ser His Gln Glu Val Ala Thr Ala Asn Leu Ala Trp Ala Ser<br>240                         245                     250                    255 | 767 |

| | | |
|---|---|---|
| GTA GCA ATA CAT CAG GTG CAG GTA TGC AGA GGC CTT GCC AAA CAG ACA<br>Val Ala Ile His Gln Val Gln Val Cys Arg Gly Leu Ala Lys Gln Thr<br>260                   265                     270 | 815 |

| | | |
|---|---|---|
| GAA TTG AAT GAC TTC CTA CTC GAC GTA TCA AAA ACA TAT TTT GAT AAC<br>Glu Leu Asn Asp Phe Leu Leu Asp Val Ser Lys Thr Tyr Phe Asp Asn<br>275                         280                     285 | 863 |

| | | |
|---|---|---|
| ATA GTT GCA ATA GAT TCT CTA CTT GAA CAC ATA ATG ATA TAT GCA AAA<br>Ile Val Ala Ile Asp Ser Leu Leu Glu His Ile Met Ile Tyr Ala Lys<br>290                   295                     300 | 911 |

| | | |
|---|---|---|
| AAC CTG GTG AAT GCC GAT CGT TGT GCA CTT TTC CAG GTG GAC CAT AAG<br>Asn Leu Val Asn Ala Asp Arg Cys Ala Leu Phe Gln Val Asp His Lys<br>305                         310                     315 | 959 |

| | | |
|---|---|---|
| AAC AAG GAG TTA TAT TCA GAC CCT TTT GAT ATT GGA GAG GAA AAG GAA<br>Asn Lys Glu Leu Tyr Ser Asp Pro Phe Asp Ile Gly Glu Glu Lys Glu<br>320                   325                     330                    335 | 1007 |

| | | |
|---|---|---|
| GGA AAA CCT GTC TTC AAG AAG ACC AAA GAG ATA AGA TTT TCA ATT GAG<br>Gly Lys Pro Val Phe Lys Lys Thr Lys Glu Ile Arg Phe Ser Ile Glu<br>                   340                     345                    350 | 1055 |

| | | |
|---|---|---|
| AAA GGA ATT GCT GGC CAA GTA GCA AGA ACA GGG GAA GTC CTG AAC ATT<br>Lys Gly Ile Ala Gly Gln Val Ala Arg Thr Gly Glu Val Leu Asn Ile<br>                   355                     360                    365 | 1103 |

| | | |
|---|---|---|
| CCA GAT GCC TAT GCA GAC CCA CGC TTT AAC AGA GAA GTA GAC TTG TAC<br>Pro Asp Ala Tyr Ala Asp Pro Arg Phe Asn Arg Glu Val Asp Leu Tyr<br>          370                     375                     380 | 1151 |

| | | |
|---|---|---|
| ACA GGC TAC ACC ACG CGG AAC ATC CTG TGC ATG CCC ATC GTC AGC CGA<br>Thr Gly Tyr Thr Thr Arg Asn Ile Leu Cys Met Pro Ile Val Ser Arg<br>385                         390                     395 | 1199 |

| | | |
|---|---|---|
| GGC AGC GTG ATA GGT GTG GTG CAG ATG GTC AAC AAA ATC AGT GGC AGT<br>Gly Ser Val Ile Gly Val Val Gln Met Val Asn Lys Ile Ser Gly Ser<br>400                         405                     410                    415 | 1247 |

| | | |
|---|---|---|
| GCC TTC TCT AAA ACA GAT GAA AAC AAC TTC AAA ATG TTT GCC GTC TTT<br>Ala Phe Ser Lys Thr Asp Glu Asn Asn Phe Lys Met Phe Ala Val Phe<br>                   420                     425                    430 | 1295 |

| | | |
|---|---|---|
| TGT GCT TTA GCC TTA CAC TGT GCT AAT ATG TAT CAT AGA ATT CGC CAC<br>Cys Ala Leu Ala Leu His Cys Ala Asn Met Tyr His Arg Ile Arg His<br>                   435                     440                    445 | 1343 |

| | | |
|---|---|---|
| TCA GAG TGC ATT TAC CGG GTA ACG ATG GAA AAG CTG TCC TAC CAT AGC<br>Ser Glu Cys Ile Tyr Arg Val Thr Met Glu Lys Leu Ser Tyr His Ser<br>          450                     455                     460 | 1391 |

| | | |
|---|---|---|
| ATT TGT ACT TCA GAA GAG TGG CAA GGT CTC ATG CAA TTC ACC CTT CCC<br>Ile Cys Thr Ser Glu Glu Trp Gln Gly Leu Met Gln Phe Thr Leu Pro<br>465                         470                     475 | 1439 |

| | | |
|---|---|---|
| GTG CGT CTC TGC AAA GAA ATT GAA TTA TTC CAC TTT GAC ATT GGT CCT<br>Val Arg Leu Cys Lys Glu Ile Glu Leu Phe His Phe Asp Ile Gly Pro<br>480                         485                     490                    495 | 1487 |

| | | |
|---|---|---|
| TTT GAA AAC ATG TGG CCT GGA ATT TTT GTC TAC ATG GTT CAT CGG TCC<br>Phe Glu Asn Met Trp Pro Gly Ile Phe Val Tyr Met Val His Arg Ser<br>                   500                     505                    510 | 1535 |

| | | |
|---|---|---|
| TGT GGG ACA TCC TGC TTT GAG CTT GAA AAG TTG TGT CGT TTT ATT ATG<br>Cys Gly Thr Ser Cys Phe Glu Leu Glu Lys Leu Cys Arg Phe Ile Met<br>                   515                     520                    525 | 1583 |

| | | |
|---|---|---|
| TCT GTG AAG AAG AAC TAT CGG CGG GTT CCT TAT CAC AAC TGG AAG CAT<br>Ser Val Lys Lys Asn Tyr Arg Arg Val Pro Tyr His Asn Trp Lys His<br>          530                     535                    540 | 1631 |

| | | |
|---|---|---|
| GCG GTC ACT GTA GCA CAC TGC ATG TAT GCC ATA CTT CAG AAC AAT CAC<br>Ala Val Thr Val Ala His Cys Met Tyr Ala Ile Leu Gln Asn Asn His<br>545                         550                     555 | 1679 |

-continued

| | | |
|---|---|---|
| ACG CTT TTC ACA GAC CTT GAG CGC AAA GGA CTG CTG ATT GCG TGT CTG<br>Thr Leu Phe Thr Asp Leu Glu Arg Lys Gly Leu Leu Ile Ala Cys Leu<br>560                 565                       570                     575 | 1727 |
| TGT CAT GAC CTG GAC CAC AGG GGC TTC AGT AAC AGC TAC CTG CAG AAG<br>Cys His Asp Leu Asp His Arg Gly Phe Ser Asn Ser Tyr Leu Gln Lys<br>580                           585                        590 | 1775 |
| TTC GAC CAC CCT CTG GCC GCT CTC TAC TCC ACT TCC ACC ATG GAG CAG<br>Phe Asp His Pro Leu Ala Ala Leu Tyr Ser Thr Ser Thr Met Glu Gln<br>595                      600                      605 | 1823 |
| CAC CAC TTC TCC CAG ACT GTG TCC ATC CTC CAG TTG GAA GGG CAC AAT<br>His His Phe Ser Gln Thr Val Ser Ile Leu Gln Leu Glu Gly His Asn<br>610                      615                     620 | 1871 |
| ATC TTC TCC ACT CTG AGC TCC AGT GAA TAT GAG CAG GTG CTT GAG ATC<br>Ile Phe Ser Thr Leu Ser Ser Ser Glu Tyr Glu Gln Val Leu Glu Ile<br>625                      630                     635 | 1919 |
| ATC CGC AAA GCC ATC ATT GCC ACA GAC CTT GCT TTA TAC TTT GGA AAC<br>Ile Arg Lys Ala Ile Ile Ala Thr Asp Leu Ala Leu Tyr Phe Gly Asn<br>640                 645                     650                     655 | 1967 |
| AGG AAG CAG TTG GAA GAG ATG TAC CAG ACC GGA TCA CTA AAC CTT AAT<br>Arg Lys Gln Leu Glu Glu Met Tyr Gln Thr Gly Ser Leu Asn Leu Asn<br>660                      665                     670 | 2015 |
| AAT CAA TCA CAT AGA GAC CGT GTA ATT GGT TTG ATG ATG ACT GCC TGT<br>Asn Gln Ser His Arg Asp Arg Val Ile Gly Leu Met Met Thr Ala Cys<br>675                      680                     685 | 2063 |
| GAC CTT TGT TCT GTG ACA AAA CTG TGG CCC GTT ACA AAA TTG ACG GCA<br>Asp Leu Cys Ser Val Thr Lys Leu Trp Pro Val Thr Lys Leu Thr Ala<br>690                      695                     700 | 2111 |
| AAT GAT ATA TAT GCA GAA TTC TGG GCT GAG GGT GAT GAA ATG AAG AAA<br>Asn Asp Ile Tyr Ala Glu Phe Trp Ala Glu Gly Asp Glu Met Lys Lys<br>705                      710                     715 | 2159 |
| TTG GGA ATA CAG CCT ATT CCT ATG ATG GAC AGA GAC AAG AAG GAT GAA<br>Leu Gly Ile Gln Pro Ile Pro Met Met Asp Arg Asp Lys Lys Asp Glu<br>720                      725                     730                     735 | 2207 |
| GTC CCC CAA GGC CAG CTT GGG TTC TAC AAT GCC GTG GCC ATT CCC TGC<br>Val Pro Gln Gly Gln Leu Gly Phe Tyr Asn Ala Val Ala Ile Pro Cys<br>740                      745                     750 | 2255 |
| TAT ACA ACC CTT ACC CAG ATC CTC CCT CCC ACG GAG CCT CTT CTG AAA<br>Tyr Thr Thr Leu Thr Gln Ile Leu Pro Pro Thr Glu Pro Leu Leu Lys<br>755                      760                     765 | 2303 |
| GCA TGC AGG GAT AAT CTC AGT CAG TGG GAG AAG GTG ATT CGA GGG GAG<br>Ala Cys Arg Asp Asn Leu Ser Gln Trp Glu Lys Val Ile Arg Gly Glu<br>770                      775                     780 | 2351 |
| GAG ACT GCA ACC TGG ATT TCA TCC CCA TCC GTG GCT CAG AAG GCA GCT<br>Glu Thr Ala Thr Trp Ile Ser Ser Pro Ser Val Ala Gln Lys Ala Ala<br>785                      790                     795 | 2399 |
| GCA TCT GAA GAT TGAGCACTGG TCACCCTGAC ACGCTGTCCC ACCTACAGAT<br>Ala Ser Glu Asp<br>800 | 2451 |
| CCTCATCTTG CTTCTTTGAC ATTCTTTTCC TTTTTTTGGG GGGGGTGGGG GGAACCTGCA | 2511 |
| CCTGGTAACT GGGGTGCAAA CCTCTTCAAG AAGGTAACAT CAAATAAATA AGTCAAGCAG | 2571 |
| AGGACTTCCT GCCAATCTCT TCTGTGAGGC ATCATAGACA CTGAGCAACC AGGACCACCC | 2631 |
| CCACGTTCAG AAATCAGCTG GCCAAGTGAC TCCATTTGAC TTGCAAACCA GCCTTTTCTA | 2691 |
| ATAGGCTAAT ATTGCTGAGG CCTTAAAGGA AATGGACAAA AATTATCCAG AAGGGGTACT | 2751 |
| TTTCCATTGT ATCTTTCTAA TAAGGGTTTA AAATGGTACT ATTATGGTAT TGTACTTGGG | 2811 |
| CTTTAACATC AATGTTGCTT TGATGTTGTT GGATATAAAT AGGAATTTTT ACACATTACT | 2871 |
| ATTGTGAATG GTGAATGTTC ATGTATGACC TACTTGTAAT TAACTTGAGT TGTAGTCCAC | 2931 |

-continued

```
AGCCTCAGGA CAAATGTCGT TGAGGTTACA GAGTAAGAAA TGATGGCAAA ACGTCAAACT      2991

CTTATTTCAG AGCTTCATGA ATTTAGTTAG ACTAAACATA ATTCTTTAAG TTCAACCTAA      3051

AGGGCTGAGA TCAATAAATT TAACACTAGA CGAAGTAGAC TTCCTGTCTT TTTGAGAAGA      3111

GATGAGGTAT ATGTTACAAT AAATCTCAGA ACTTCAAGTA GCAGTTCAAA AGATGTCAGT      3171

TTTTAAAATT GTTTTTGTTG TTGTCTTGGC AGTTTTACTG AACCCTTTGC ATAAAGAACA      3231

AAATAAAAGC TCGGCATTGT AATTTTTTTA ATGGACAAGT CTTATGGATA CGAAGGGTAC      3291

ATTTTTCATA ATGATTCCTT TATATTTTCA CTTTGTGTCA TTGCAGAATT TTAGACTCTC      3351

ATTCACAATG AAAAGTTTAT TTTAAACATT GTTTAATTAA AATACCATAC AGTTCTCTTT      3411

TAAACATCAA ACCATAAAAA GTGTATTTTG TAATTTTACT CTGACCTGCC GCAGTCACCT      3471

CTCACTTATC TCTTCCACGT ACTGCACGGT CGTATTTCAT GAGCTTTCTG TCCATAGCAC      3531

AGAAACAGAG CAGAAAGTAG TACAATCATG TTGGACCTTC TTTCTGTTCT CTTTACTCTT      3591

CTCACAGATC AGATCACTCC ATAGAAGCCT GTGGGTTTCG ATGGTTTCTT CTATACACCT      3651

TTTTGGTTGA CCAGTATTAC TATACAATGT AAGTGTTTTA AAAAATACGA AAGTAATACT      3711

CTGCACCCCT TCCTACAAAG ATGATAAAGC AGTCACTTCT GGCGCATTTT AATAATTTAA      3771

AGATTTTTAG TGCAATGGCA CGGTAACCTC CAAACCTGAA TTAGACAGAG ACTCACTCAG      3831

GAAGTGACAG GCCCATCATA TCAAATAACT TATTCACTTT TCATGTGGCA GGAAACTGGA      3891

ATATCGCTTT TAATAAAATG GAAAATATG CTTCTACATA TTTACCACCA TAGGCGTTTT      3951

GTTCATATGA GCCTGGTTTG TGCAAAATTA AATCAGAGGC TTCTACAACA TGGTTTATTT      4011

ATGTTGTAGC AAAGTTGGCT CTACATAAAC ATTGTTCTTA TTTTAAAATT AACACTATGT      4071

GTTCAGTTTT CTTGTGGGCT TCTGAAAGTT GCCATCTTCC CTCCGTGGAG CTCCATTTGC      4131

TATTTTCATT ATACACTATG AGGTAAAATG TAATAACAAA AGAGAGAGAA GTACCACTGT      4191

GGCTAGATAT ATACACACAC ATATATATAT GGATGGATGT AATATATGTA GAACACACAC      4251

ATAGATGTAT ATAGGATACA CACTCATGTA TGTAAACGTA TACATATGTG TATATATGAT      4311

ACATACACAT ACACACACAC GAGAGACAGA AGGAAAGAGA GGAAGAGAGA AGCAAACATG      4371

TAGGAAAAAA TATAAATC                                                   4389
```

(2) INFORMATION FOR SEQ ID NO:4:

(i) SEQUENCE CHARACTERISTICS:
        (A) LENGTH: 803 amino acids
        (B) TYPE: amino acid
        (D) TOPOLOGY: linear (ii) MOLECULE TYPE: protein (xi) SEQUENCE DESCRIPTION: SEQ ID NO:4:

```
Phe Ala Leu Ala Ala Ala Ala Ala Leu Leu Phe Gly Ser Asp Met Glu
 1               5                  10                  15

Asp Gly Pro Ser Asn Asn Ala Ser Cys Phe Arg Leu Thr Glu Cys
            20                  25                  30

Phe Leu Ser Pro Ser Leu Thr Asp Glu Lys Val Lys Ala Tyr Leu Ser
        35                  40                  45

Leu His Pro Gln Val Leu Asp Glu Phe Val Ser Glu Ser Val Ser Ala
    50                  55                  60

Glu Thr Val Glu Lys Trp Leu Lys Arg Lys Asn Asn Lys Ser Glu Asp
65                  70                  75                  80

Glu Ser Ala Pro Lys Glu Val Ser Arg Tyr Gln Asp Thr Asn Met Gln
                85                  90                  95
```

-continued

```
Gly Val Val Tyr Glu Leu Asn Ser Tyr Ile Glu Gln Arg Leu Asp Thr
                100                 105                 110
Gly Gly Asp Asn Gln Leu Leu Leu Tyr Glu Leu Ser Ser Ile Ile Lys
            115                 120                 125
Ile Ala Thr Lys Ala Asp Gly Phe Ala Leu Tyr Phe Leu Gly Glu Cys
130                 135                 140
Asn Asn Ser Leu Cys Ile Phe Thr Pro Pro Gly Ile Lys Glu Gly Lys
145                 150                 155                 160
Pro Arg Leu Ile Pro Ala Gly Pro Ile Thr Gln Gly Thr Thr Val Ser
                165                 170                 175
Ala Tyr Val Ala Lys Ser Arg Lys Thr Leu Leu Val Glu Asp Ile Leu
            180                 185                 190
Gly Asp Glu Arg Phe Pro Arg Gly Thr Gly Leu Glu Ser Gly Thr Arg
        195                 200                 205
Ile Gln Ser Val Leu Cys Leu Pro Ile Val Thr Ala Ile Gly Asp Leu
210                 215                 220
Ile Gly Ile Leu Glu Leu Tyr Arg His Trp Gly Lys Glu Ala Phe Cys
225                 230                 235                 240
Leu Ser His Gln Glu Val Ala Thr Ala Asn Leu Ala Trp Ala Ser Val
                245                 250                 255
Ala Ile His Gln Val Gln Val Cys Arg Gly Leu Ala Lys Gln Thr Glu
            260                 265                 270
Leu Asn Asp Phe Leu Leu Asp Val Ser Lys Thr Tyr Phe Asp Asn Ile
        275                 280                 285
Val Ala Ile Asp Ser Leu Leu Glu His Ile Met Ile Tyr Ala Lys Asn
290                 295                 300
Leu Val Asn Ala Asp Arg Cys Ala Leu Phe Gln Val Asp His Lys Asn
305                 310                 315                 320
Lys Glu Leu Tyr Ser Asp Pro Phe Asp Ile Gly Glu Glu Lys Glu Gly
                325                 330                 335
Lys Pro Val Phe Lys Lys Thr Lys Glu Ile Arg Phe Ser Ile Glu Lys
            340                 345                 350
Gly Ile Ala Gly Gln Val Ala Arg Thr Gly Glu Val Leu Asn Ile Pro
        355                 360                 365
Asp Ala Tyr Ala Asp Pro Arg Phe Asn Arg Glu Val Asp Leu Tyr Thr
370                 375                 380
Gly Tyr Thr Thr Arg Asn Ile Leu Cys Met Pro Ile Val Ser Arg Gly
385                 390                 395                 400
Ser Val Ile Gly Val Val Gln Met Val Asn Lys Ile Ser Gly Ser Ala
                405                 410                 415
Phe Ser Lys Thr Asp Glu Asn Asn Phe Lys Met Phe Ala Val Phe Cys
            420                 425                 430
Ala Leu Ala Leu His Cys Ala Asn Met Tyr His Arg Ile Arg His Ser
        435                 440                 445
Glu Cys Ile Tyr Arg Val Thr Met Glu Lys Leu Ser Tyr His Ser Ile
450                 455                 460
Cys Thr Ser Glu Glu Trp Gln Gly Leu Met Gln Phe Thr Leu Pro Val
465                 470                 475                 480
Arg Leu Cys Lys Glu Ile Glu Leu Phe His Phe Asp Ile Gly Pro Phe
                485                 490                 495
Glu Asn Met Trp Pro Gly Ile Phe Val Tyr Met Val His Arg Ser Cys
            500                 505                 510
Gly Thr Ser Cys Phe Glu Leu Glu Lys Leu Cys Arg Phe Ile Met Ser
        515                 520                 525
```

```
Val Lys Lys Asn Tyr Arg Arg Val Pro Tyr His Asn Trp Lys His Ala
    530                 535                 540

Val Thr Val Ala His Cys Met Tyr Ala Ile Leu Gln Asn Asn His Thr
545                 550                 555                 560

Leu Phe Thr Asp Leu Glu Arg Lys Gly Leu Leu Ile Ala Cys Leu Cys
            565                 570                 575

His Asp Leu Asp His Arg Gly Phe Ser Asn Ser Tyr Leu Gln Lys Phe
        580                 585                 590

Asp His Pro Leu Ala Ala Leu Tyr Ser Thr Ser Met Glu Gln His
    595                 600                 605

His Phe Ser Gln Thr Val Ser Ile Leu Gln Leu Glu Gly His Asn Ile
    610                 615                 620

Phe Ser Thr Leu Ser Ser Ser Glu Tyr Glu Gln Val Leu Glu Ile Ile
625                 630                 635                 640

Arg Lys Ala Ile Ile Ala Thr Asp Leu Ala Leu Tyr Phe Gly Asn Arg
                645                 650                 655

Lys Gln Leu Glu Glu Met Tyr Gln Thr Gly Ser Leu Asn Leu Asn Asn
            660                 665                 670

Gln Ser His Arg Asp Arg Val Ile Gly Leu Met Met Thr Ala Cys Asp
        675                 680                 685

Leu Cys Ser Val Thr Lys Leu Trp Pro Val Thr Lys Leu Thr Ala Asn
690                 695                 700

Asp Ile Tyr Ala Glu Phe Trp Ala Glu Gly Asp Glu Met Lys Lys Leu
705                 710                 715                 720

Gly Ile Gln Pro Ile Pro Met Met Asp Arg Asp Lys Lys Asp Glu Val
                725                 730                 735

Pro Gln Gly Gln Leu Gly Phe Tyr Asn Ala Val Ala Ile Pro Cys Tyr
            740                 745                 750

Thr Thr Leu Thr Gln Ile Leu Pro Pro Thr Glu Pro Leu Leu Lys Ala
        755                 760                 765

Cys Arg Asp Asn Leu Ser Gln Trp Glu Lys Val Ile Arg Gly Glu Glu
770                 775                 780

Thr Ala Thr Trp Ile Ser Ser Pro Ser Val Ala Gln Lys Ala Ala Ala
785                 790                 795                 800

Ser Glu Asp (2) INFORMATION FOR SEQ ID NO:5:

(i) SEQUENCE CHARACTERISTICS:
        (A) LENGTH: 3195 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 67..2403

(xi) SEQUENCE DESCRIPTION: SEQ ID NO:5:

CATCCACAGA GATGTTACAG TTGAAGAGAT GGGGGTAGAG AAGACTTTGA AGGAAAAGAA      60

TGTAGA ATG AGG ATA GAA GAG AGG AAA TCC CAA CAT TTA ACA GGT TTG        108
       Met Arg Ile Glu Glu Arg Lys Ser Gln His Leu Thr Gly Leu
         1               5                  10

ACA GAT GAA AAA GTG AAG GCA TAT CTT TCT CTT CAC CCC CAG GTA TTA       156
Thr Asp Glu Lys Val Lys Ala Tyr Leu Ser Leu His Pro Gln Val Leu
 15                  20                  25                  30
```

```
GAT GAA TTT GTA TCT GAA AGT GTT AGT GCA GAG ACA GTA GAG AAA TGG      204
Asp Glu Phe Val Ser Glu Ser Val Ser Ala Glu Thr Val Glu Lys Trp
             35                  40                  45

CTG AAG AGG AAG AAC AAC AAA TCA GAA GAT GAA TCG GCT CCT AAG GAA      252
Leu Lys Arg Lys Asn Asn Lys Ser Glu Asp Glu Ser Ala Pro Lys Glu
         50                  55                  60

GTC AGC AGG TAC CAA GAT ACG AAT ATG CAG GGA GTT GTA TAT GAA CTA      300
Val Ser Arg Tyr Gln Asp Thr Asn Met Gln Gly Val Val Tyr Glu Leu
             65                  70                  75

AAC AGC TAT ATA GAA CAA CGG TTG GAC ACA GGA GAC AAC CAG CTA          348
Asn Ser Tyr Ile Glu Gln Arg Leu Asp Thr Gly Gly Asp Asn Gln Leu
         80                  85                  90

CTC CTC TAT GAA CTG AGC AGC ATC ATT AAA ATA GCC ACA AAA GCC GAT      396
Leu Leu Tyr Glu Leu Ser Ser Ile Ile Lys Ile Ala Thr Lys Ala Asp
 95                 100                 105                 110

GGA TTT GCA CTG TAT TTC CTT GGA GAG TGC AAT AAT AGC CTG TGT ATA      444
Gly Phe Ala Leu Tyr Phe Leu Gly Glu Cys Asn Asn Ser Leu Cys Ile
             115                 120                 125

TTC ACG CCA CCT GGG ATA AAG GAA GGA AAA CCC CGC CTC ATC CCT GCT      492
Phe Thr Pro Pro Gly Ile Lys Glu Gly Lys Pro Arg Leu Ile Pro Ala
         130                 135                 140

GGG CCC ATC ACT CAG GGC ACC ACC GTC TCT GCT TAT GTG GCC AAG TCC      540
Gly Pro Ile Thr Gln Gly Thr Thr Val Ser Ala Tyr Val Ala Lys Ser
             145                 150                 155

AGG AAA ACA CTG CTA GTA GAA GAC ATC CTT GGA GAT GAA CGA TTT CCA      588
Arg Lys Thr Leu Leu Val Glu Asp Ile Leu Gly Asp Glu Arg Phe Pro
         160                 165                 170

AGA GGT ACT GGA CTG GAA TCA GGG ACT CGT ATC CAG TCT GTT CTT TGC      636
Arg Gly Thr Gly Leu Glu Ser Gly Thr Arg Ile Gln Ser Val Leu Cys
175                 180                 185                 190

TTA CCA ATT GTC ACT GCA ATT GGT GAC TTG ATT GGT ATT CTC GAG CTG      684
Leu Pro Ile Val Thr Ala Ile Gly Asp Leu Ile Gly Ile Leu Glu Leu
             195                 200                 205

TAT CGG CAC TGG GGC AAA GAA GCC TTC TGT CTT AGT CAC CAG GAG GTT      732
Tyr Arg His Trp Gly Lys Glu Ala Phe Cys Leu Ser His Gln Glu Val
         210                 215                 220

GCA ACA GCA AAT CTT GCC TGG GCT TCA GTA GCA ATA CAT CAG GTG CAG      780
Ala Thr Ala Asn Leu Ala Trp Ala Ser Val Ala Ile His Gln Val Gln
             225                 230                 235

GTA TGC AGA GGC CTT GCC AAA CAG ACA GAA TTG AAT GAC TTC CTA CTC      828
Val Cys Arg Gly Leu Ala Lys Gln Thr Glu Leu Asn Asp Phe Leu Leu
         240                 245                 250

GAC GTA TCA AAA ACA TAT TTT GAT AAC ATA GTT GCA ATA GAT TCT CTA      876
Asp Val Ser Lys Thr Tyr Phe Asp Asn Ile Val Ala Ile Asp Ser Leu
255                 260                 265                 270

CTT GAA CAC ATA ATG ATA TAT GCA AAA AAC CTG GTG AAT GCC GAT CGT      924
Leu Glu His Ile Met Ile Tyr Ala Lys Asn Leu Val Asn Ala Asp Arg
             275                 280                 285

TGT GCA CTT TTC CAG GTG GAC CAT AAG AAC AAG GAG TTA TAT TCA GAC      972
Cys Ala Leu Phe Gln Val Asp His Lys Asn Lys Glu Leu Tyr Ser Asp
         290                 295                 300

CTT TTT GAT ATT GGA GAG GAA AAG GAA GGA AAA CCT GTC TTC AAG AAG      1020
Leu Phe Asp Ile Gly Glu Glu Lys Glu Gly Lys Pro Val Phe Lys Lys
             305                 310                 315

ACC AAA GAG ATA AGA TTT TCA ATT GAG AAA GGA ATT GCT GGC CAA GTA      1068
Thr Lys Glu Ile Arg Phe Ser Ile Glu Lys Gly Ile Ala Gly Gln Val
         320                 325                 330

GCA AGA ACA GGG GAA GTC CTG AAC ATT CCA GAT GCC TAT GCA GAC CCA      1116
Ala Arg Thr Gly Glu Val Leu Asn Ile Pro Asp Ala Tyr Ala Asp Pro
335                 340                 345                 350
```

```
CGC TTT AAC AGA GAA GTA GAC TTG TAC ACA GGC TAC ACC ACG CGG AAC      1164
Arg Phe Asn Arg Glu Val Asp Leu Tyr Thr Gly Tyr Thr Thr Arg Asn
                355                 360                 365

ATC CTG TGC ATG CCC ATC GTC AGC CGA GGC AGC GTG ATA GGT GTG GTG      1212
Ile Leu Cys Met Pro Ile Val Ser Arg Gly Ser Val Ile Gly Val Val
            370                 375                 380

CAG ATG GTC AAC AAA ATC AGT GGC AGT GCC TTC TCT AAA ACA GAT GAA      1260
Gln Met Val Asn Lys Ile Ser Gly Ser Ala Phe Ser Lys Thr Asp Glu
                385                 390                 395

AAC AAC TTC AAA ATG TTT GCC GTC TTT TGT GCT TTA GCC TTA CAC TGT      1308
Asn Asn Phe Lys Met Phe Ala Val Phe Cys Ala Leu Ala Leu His Cys
            400                 405                 410

GCT AAT ATG TAT CAT AGA ATT CGC CAC TCA GAG TGC ATT TAC CGG GTA      1356
Ala Asn Met Tyr His Arg Ile Arg His Ser Glu Cys Ile Tyr Arg Val
415                 420                 425                 430

ACG ATG GAA AAG CTG TCC TAC CAT AGC ATT TGT ACT TCA GAA GAG TGG      1404
Thr Met Glu Lys Leu Ser Tyr His Ser Ile Cys Thr Ser Glu Glu Trp
                435                 440                 445

CAA GGT CTC ATG CAA TTC ACC CTT CCC GTG CGT CTC TGC AAA GAA ATT      1452
Gln Gly Leu Met Gln Phe Thr Leu Pro Val Arg Leu Cys Lys Glu Ile
            450                 455                 460

GAA TTA TTC CAC TTT GAC ATT GGT CCT TTT GAA AAC ATG TGG CCT GGA      1500
Glu Leu Phe His Phe Asp Ile Gly Pro Phe Glu Asn Met Trp Pro Gly
                465                 470                 475

ATT TTT GTC TAC ATG GTT CAT CGG TCC TGT GGG ACA TCC TGC TTT GAG      1548
Ile Phe Val Tyr Met Val His Arg Ser Cys Gly Thr Ser Cys Phe Glu
            480                 485                 490

CTT GAA AAG TTG TGT CGT TTT ATT ATG TCT GTG AAG AAG AAC TAT CGG      1596
Leu Glu Lys Leu Cys Arg Phe Ile Met Ser Val Lys Lys Asn Tyr Arg
495                 500                 505                 510

CGG GTT CCT TAT CAC AAC TGG AAG CAT GCG GTC ACT GTA GCA CAC TGC      1644
Arg Val Pro Tyr His Asn Trp Lys His Ala Val Thr Val Ala His Cys
                515                 520                 525

ATG TAT GCC ATA CTT CAG AAC AAT CAC ACG CTT TTC ACA GAC CTT GAG      1692
Met Tyr Ala Ile Leu Gln Asn Asn His Thr Leu Phe Thr Asp Leu Glu
            530                 535                 540

CGC AAA GGA CTG CTG ATT GCG TGT CTG TGT CAT GAC CTG GAC CAC AGG      1740
Arg Lys Gly Leu Leu Ile Ala Cys Leu Cys His Asp Leu Asp His Arg
                545                 550                 555

GGC TTC AGT AAC AGC TAC CTG CAG AAG TTC GAC CAC CCT CTG GCC GCT      1788
Gly Phe Ser Asn Ser Tyr Leu Gln Lys Phe Asp His Pro Leu Ala Ala
            560                 565                 570

CTC TAC TCC ACT TCC ACC ATG GAG CAG CAC CAC TTC TCC CAG ACT GTG      1836
Leu Tyr Ser Thr Ser Thr Met Glu Gln His His Phe Ser Gln Thr Val
575                 580                 585                 590

TCC ATC CTC CAG TTG GAA GGG CAC AAT ATC TTC TCC ACT CTG AGC TCC      1884
Ser Ile Leu Gln Leu Glu Gly His Asn Ile Phe Ser Thr Leu Ser Ser
                595                 600                 605

AGT GAA TAT GAG CAG GTG CTT GAG ATC ATC CGC AAA GCC ATC ATT GCC      1932
Ser Glu Tyr Glu Gln Val Leu Glu Ile Ile Arg Lys Ala Ile Ile Ala
            610                 615                 620

ACA GAC CTT GCT TTA TAC TTT GGA AAC AGG AAG CAG TTG GAA GAG ATG      1980
Thr Asp Leu Ala Leu Tyr Phe Gly Asn Arg Lys Gln Leu Glu Glu Met
            625                 630                 635

TAC CAG ACC GGA TCA CTA AAC CTT AAT AAT CAA TCA CAT AGA GAC CGT      2028
Tyr Gln Thr Gly Ser Leu Asn Leu Asn Asn Gln Ser His Arg Asp Arg
                640                 645                 650

GTA ATT GGT TTG ATG ATG ACT GCC TGT GAC CTT TGT TCT GTG ACA AAA      2076
Val Ile Gly Leu Met Met Thr Ala Cys Asp Leu Cys Ser Val Thr Lys
655                 660                 665                 670
```

```
CTG TGG CCC GTT ACA AAA TTG ACG GCA AAT GAT ATA TAT GCA GAA TTC      2124
Leu Trp Pro Val Thr Lys Leu Thr Ala Asn Asp Ile Tyr Ala Glu Phe
                675                 680                 685

TGG GCT GAG GGT GAT GAA ATG AAG AAA TTG GGA ATA CAG CCT ATT CCT      2172
Trp Ala Glu Gly Asp Glu Met Lys Lys Leu Gly Ile Gln Pro Ile Pro
            690                 695                 700

ATG ATG GAC AGA GAC AAG AAG GAT GAA GTC CCC CAA GGC CAG CTT GGG      2220
Met Met Asp Arg Asp Lys Lys Asp Glu Val Pro Gln Gly Gln Leu Gly
                705                 710                 715

TTC TAC AAT GCC GTG GCC ATT CCC TGC TAT ACA ACC CTT ACC CAG ATC      2268
Phe Tyr Asn Ala Val Ala Ile Pro Cys Tyr Thr Thr Leu Thr Gln Ile
        720                 725                 730

CTC CCT CCC ACG GAG CCT CTT CTG AAA GCA TGC AGG GAT AAT CTC AGT      2316
Leu Pro Pro Thr Glu Pro Leu Leu Lys Ala Cys Arg Asp Asn Leu Ser
735                 740                 745                 750

CAG TGG GAG AAG GTG ATT CGA GGG GAG GAG ACT GCA ACC TGG ATT TCA      2364
Gln Trp Glu Lys Val Ile Arg Gly Glu Glu Thr Ala Thr Trp Ile Ser
                755                 760                 765

TCC CCA TCC GTG GCT CAG AAG GCA GCT GCA TCT GAA GAT TGAGCACTGG       2413
Ser Pro Ser Val Ala Gln Lys Ala Ala Ala Ser Glu Asp
                770                 775

TCACCCTGAC ACGCTGTCCC ACCTACAGAT CCTCATCTTG CTTCTTTGAC ATTCTTTTCC    2473

TTTTTTTGGG GGGGGTGGGG GGAACCTGCA CCTGGTAACT GGGGTGCAAA CCTCTTCAAG    2533

AAGGTAACAT CAAATAAATA AGTCAAGCAG AGGACTTCCT GGAATTCCAA TCCCAACACT    2593

TTGGGAGGCT GAGGTGGGTG GATCACCTGA GGTCTAGAGT TCGAGACTGG ACTGGGCAAG    2653

ATGGTGAAAC TCTGTCTCTA CTAAAAATAC AAAAATACAA AATTAGCTGG GTGTGGTGGT    2713

TGCATGCCTG TAGTTCGGGA GGCTGAGGTA GGAGAATCAC TTGAACCTGG GGGTGGAGG    2773

CTGAAGTGAG CCAAGGTCGT GTCAGTGCAC TCCAGCCTAG ACAACAGAAC AAGACTCTGT    2833

CTCAAAAAAA AAAAAAGTA TATCCTACAA ATGCTAATTA ATTTTTTCCC ACTAGCTAAT     2893

TGGTTTATGA ATAAGAAAGA TGTTAAAAAA TGATGACAAA TGCAGTCGGT TACAGTGGCT    2953

CATGCCTGTG ATCCCAGCAC TTTGGGAGGC CGAGGCGGGT GGATCATGAG GTCAAGAGAT    3013

CGAGACCATC CTGGCCAACA TGGTGAAACC CCGTCTCTAC TGAAAAAAAA AAAAAATTAG    3073

CTGGGCGTGG TGTGCATAGT GGTGTAATTC CAGCTACTCT GGAGGCTGAG GCAGGAGAAT    3133

CGCTTGAACC CAGGAGGCAG AGGTTGCAGT GAGCCAGGAT GGTGGAATTC CTGCAGCCCG    3193

GG                                                                  3195
```

(2) INFORMATION FOR SEQ ID NO:6:

(i) SEQUENCE CHARACTERISTICS:
        (A) LENGTH: 779 amino acids
        (B) TYPE: amino acid
        (D) TOPOLOGY: linear (ii) MOLECULE TYPE: protein (xi) SEQUENCE DESCRIPTION: SEQ ID NO:6:

```
Met Arg Ile Glu Glu Arg Lys Ser Gln His Leu Thr Gly Leu Thr Asp
1               5                   10                  15

Glu Lys Val Lys Ala Tyr Leu Ser Leu His Pro Gln Val Leu Asp Glu
                20                  25                  30

Phe Val Ser Glu Ser Val Ser Ala Glu Thr Val Glu Lys Trp Leu Lys
            35                  40                  45

Arg Lys Asn Asn Lys Ser Glu Asp Glu Ser Ala Pro Lys Glu Val Ser
        50                  55                  60
```

```
Arg Tyr Gln Asp Thr Asn Met Gln Gly Val Val Tyr Glu Leu Asn Ser
 65                  70                  75                  80

Tyr Ile Glu Gln Arg Leu Asp Thr Gly Gly Asp Asn Gln Leu Leu Leu
                 85                  90                  95

Tyr Glu Leu Ser Ser Ile Ile Lys Ile Ala Thr Lys Ala Asp Gly Phe
            100                 105                 110

Ala Leu Tyr Phe Leu Gly Glu Cys Asn Asn Ser Leu Cys Ile Phe Thr
        115                 120                 125

Pro Pro Gly Ile Lys Glu Gly Lys Pro Arg Leu Ile Pro Ala Gly Pro
    130                 135                 140

Ile Thr Gln Gly Thr Thr Val Ser Ala Tyr Val Ala Lys Ser Arg Lys
145                 150                 155                 160

Thr Leu Leu Val Glu Asp Ile Leu Gly Asp Glu Arg Phe Pro Arg Gly
                165                 170                 175

Thr Gly Leu Glu Ser Gly Thr Arg Ile Gln Ser Val Leu Cys Leu Pro
            180                 185                 190

Ile Val Thr Ala Ile Gly Asp Leu Ile Gly Ile Leu Glu Leu Tyr Arg
        195                 200                 205

His Trp Gly Lys Glu Ala Phe Cys Leu Ser His Gln Glu Val Ala Thr
    210                 215                 220

Ala Asn Leu Ala Trp Ala Ser Val Ala Ile His Gln Val Gln Val Cys
225                 230                 235                 240

Arg Gly Leu Ala Lys Gln Thr Glu Leu Asn Asp Phe Leu Leu Asp Val
                245                 250                 255

Ser Lys Thr Tyr Phe Asp Asn Ile Val Ala Ile Asp Ser Leu Leu Glu
            260                 265                 270

His Ile Met Ile Tyr Ala Lys Asn Leu Val Asn Ala Asp Arg Cys Ala
        275                 280                 285

Leu Phe Gln Val Asp His Lys Asn Lys Glu Leu Tyr Ser Asp Leu Phe
    290                 295                 300

Asp Ile Gly Glu Glu Lys Glu Gly Lys Pro Val Phe Lys Lys Thr Lys
305                 310                 315                 320

Glu Ile Arg Phe Ser Ile Glu Lys Gly Ile Ala Gly Gln Val Ala Arg
                325                 330                 335

Thr Gly Glu Val Leu Asn Ile Pro Asp Ala Tyr Ala Asp Pro Arg Phe
            340                 345                 350

Asn Arg Glu Val Asp Leu Tyr Thr Gly Tyr Thr Thr Arg Asn Ile Leu
        355                 360                 365

Cys Met Pro Ile Val Ser Arg Gly Ser Val Ile Gly Val Val Gln Met
    370                 375                 380

Val Asn Lys Ile Ser Gly Ser Ala Phe Ser Lys Thr Asp Glu Asn Asn
385                 390                 395                 400

Phe Lys Met Phe Ala Val Phe Cys Ala Leu Ala Leu His Cys Ala Asn
                405                 410                 415

Met Tyr His Arg Ile Arg His Ser Glu Cys Ile Tyr Arg Val Thr Met
            420                 425                 430

Glu Lys Leu Ser Tyr His Ser Ile Cys Thr Ser Glu Glu Trp Gln Gly
        435                 440                 445

Leu Met Gln Phe Thr Leu Pro Val Arg Leu Cys Lys Glu Ile Glu Leu
    450                 455                 460

Phe His Phe Asp Ile Gly Pro Phe Glu Asn Met Trp Pro Gly Ile Phe
465                 470                 475                 480
```

```
Val Tyr Met Val His Arg Ser Cys Gly Thr Ser Cys Phe Glu Leu Glu
            485                 490                 495
Lys Leu Cys Arg Phe Ile Met Ser Val Lys Asn Tyr Arg Arg Val
        500                 505                 510
Pro Tyr His Asn Trp Lys His Ala Val Thr Val Ala His Cys Met Tyr
        515                 520                 525
Ala Ile Leu Gln Asn Asn His Thr Leu Phe Thr Asp Leu Glu Arg Lys
530                 535                 540
Gly Leu Leu Ile Ala Cys Leu Cys His Asp Leu Asp His Arg Gly Phe
545                 550                 555                 560
Ser Asn Ser Tyr Leu Gln Lys Phe Asp His Pro Leu Ala Ala Leu Tyr
                565                 570                 575
Ser Thr Ser Thr Met Glu Gln His His Phe Ser Gln Thr Val Ser Ile
            580                 585                 590
Leu Gln Leu Glu Gly His Asn Ile Phe Ser Thr Leu Ser Ser Ser Glu
            595                 600                 605
Tyr Glu Gln Val Leu Glu Ile Ile Arg Lys Ala Ile Ile Ala Thr Asp
610                 615                 620
Leu Ala Leu Tyr Phe Gly Asn Arg Lys Gln Leu Glu Glu Met Tyr Gln
625                 630                 635                 640
Thr Gly Ser Leu Asn Leu Asn Asn Gln Ser His Arg Asp Arg Val Ile
                645                 650                 655
Gly Leu Met Met Thr Ala Cys Asp Leu Cys Ser Val Thr Lys Leu Trp
            660                 665                 670
Pro Val Thr Lys Leu Thr Ala Asn Asp Ile Tyr Ala Glu Phe Trp Ala
            675                 680                 685
Glu Gly Asp Glu Met Lys Lys Leu Gly Ile Gln Pro Ile Pro Met Met
            690                 695                 700
Asp Arg Asp Lys Lys Asp Glu Val Pro Gln Gly Gln Leu Gly Phe Tyr
705                 710                 715                 720
Asn Ala Val Ala Ile Pro Cys Tyr Thr Thr Leu Thr Gln Ile Leu Pro
                725                 730                 735
Pro Thr Glu Pro Leu Leu Lys Ala Cys Arg Asp Asn Leu Ser Gln Trp
                740                 745                 750
Glu Lys Val Ile Arg Gly Glu Glu Thr Ala Thr Trp Ile Ser Ser Pro
            755                 760                 765
Ser Val Ala Gln Lys Ala Ala Ala Ser Glu Asp
770                 775

(2) INFORMATION FOR SEQ ID NO:7:

(i) SEQUENCE CHARACTERISTICS:
        (A) LENGTH: 458 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

ATTCGGCACG GGCTGCGGCC AGAGGGTGGT CGAACTTCTG CAGGTAACTG TTACTGAGCC      60

CCTGTGGTCC AGGTCATGAC ACAGACACGC AATCAGCAGT CCTTTGCGCT CAAGGTCTGT    120

GAAAAGCGTG TGATTGTTCT GAAGTATGGC ATACATGCAG TGTGCTACAG TGACCGCATG    180

CTTCCAGTTG TGATAAGGAA CCCGCCGATA GTTCTTCTTC ACAGACATAA TAAAACGACA    240

CAACTTTTCA AGCTCAAAGC AGGATGTCCC ACAGGCCCGA TGAACCATGT AGACAAAAAT    300
```

```
TCCAGGCCAC ATGTTTTCAA AAGGACCAAT GTCAAAGTGG AATAATTCAA TTTCTTTGGC      360

AGAGACGCAC CGGGAAAGGG TGAATTTGCA TGAGACCTTT GGCCACTCTT CTGAAAGTAC      420

AAATGCTATG GTAGGACAGC TTTTTCCGTC GGTTACCC                              458
```

(2) INFORMATION FOR SEQ ID NO:8:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
His Asp Xaa Xaa His Xaa Gly Xaa Xaa Xaa Xaa Xaa Xaa Xaa Xaa
1               5                   10                  15

Xaa Xaa Xaa Xaa Ala
            20
```

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GGAAACAGCT ATGACCATG                                                   19
```

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
ACTCTCCAAG GAAATACAG                                                   19
```

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
CTGTCTCTGC ACTAACAC                                                    18
```

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

TTGGCAAGGC CTCTGCAT                                                        18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CCTCTATGAA CTGAGCAG                                                        18

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GAAGGCACTG CCACTGAT                                                        18

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

TCGAGCTGTA TCGGCACT                                                        18

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

AGCGTGTGAT TGTTCTGAA                                                       19

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TGCTGGCCAA GTAGCAAG                                                        18

(2) INFORMATION FOR SEQ ID NO:18:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:18:

AAGGTCACAG GCAGTCAT                                                18

(2) INFORMATION FOR SEQ ID NO:19:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:19:

GAAGAGTGGC AAGGTCTC                                                18

(2) INFORMATION FOR SEQ ID NO:20:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:20:

TCATGACCTG GACCACCAG                                               19

(2) INFORMATION FOR SEQ ID NO:21:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:21:

CCTTCTTGAA GAGGTTTGC                                               19

(2) INFORMATION FOR SEQ ID NO:22:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:22:

ATGACTGCCT GTGACCTT                                                18

(2) INFORMATION FOR SEQ ID NO:23:

(i) SEQUENCE CHARACTERISTICS:
       (A) LENGTH: 19 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

CTGCTATACA ACCCTTACC                                                    19

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

GCTAATATTG CTGAGGCC                                                     18

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

TAAGTGAGAG GTGACTGC                                                     18

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

CCTAAAGGGC TGAGATCA                                                     18

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

CGCAGTCACC TCTCACTT                                                     18

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

TGTAAAACGA CGGCCAGT                                                         18

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

ACAAAACGCC TATGGTGG                                                         18

(2) INFORMATION FOR SEQ ID NO:30:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

TTGATCTCAG CCCTTTAGC                                                        19

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

TCATGTGGCA GGAAACTG                                                         18

(2) INFORMATION FOR SEQ ID NO:32:

(i) SEQUENCE CHARACTERISTICS:
        (A) LENGTH: 484 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

GCACGAGACC AGTATTACTA TACAATGTAA GTGTTTTAAA AAATACGAAA GTAATACTCT            60

GCACCCCTTC CTACAAAGAT GATAAAGCAG TCACTTCTGG CGCATTTTAA TAATTTAAAG           120

ATTTTTAGTG CAATGGCACG GTAACCTCCA AACCTGAATT AGACAGAGAC TCACTCAGGA           180

AGTGACAGGC CCATCATATC AAATAACTTA TTCACTTTTC ATGTGGCAGG AAACTGGAAT           240

ATCGCTTTTA ATAAAATGGA AAATATGCT TCTACATATT TACCACCATA GGCGTTTTGT            300

TCATATGAGC CTGGTTTGTG CAAAATTAAA TCAGAGGCTT CTACACATGG TTTATTTATG           360

TTGTAGCAAA GTTGGCTCTA CATAAACATT GTTCTTATTT TAAAATTAAC ACTATGTGTT           420

CGTTTTTCTT GTGGGCTTCT GAAAGTTGCC ATCTTCCCTC CGTGGAGCTC CATTTGCTAT           480

TTTC                                                                       484

(2) INFORMATION FOR SEQ ID NO:33:

(i) SEQUENCE CHARACTERISTICS:
        (A) LENGTH: 404 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

```
CTTGAACACA TCATGATATA TGCAAAAAAT CTAGTGAACG CCGACCGCTG CGCGCTCTTC     60

CAGGTGGACC ACAAGAACAA GGAGCTGTAC TCGGACCTGT TTGACATTGG GGAGGAGAAG    120

GAGGGGAAGC CCGTTTTCAA GAAGACCAAG GAGATCAGAT TTTCCATTGA GAAAGGGATT    180

GCTGGTCAAG TGGCAAGAAC GGGAGAAGTC CTGAACATTC CTGATGCCTA CGCAGACCCG    240

CGCTTTAACA GGGAGGTGGA CCTGTACACA GGCTATACCA CGCGGAACAT TCTGTGTATG    300

CCCATAGTGA GCCGCGGCAT TTGATTCGGT GTGGTGCAAA TGGTTTAACA AGATCAGCGG    360

CAGGCCTTTC AAGACGGAT GAGAACAACT TCAAGATGTT TTGC                     404
```

(2) INFORMATION FOR SEQ ID NO:34:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

```
Asp Lys Asp Asp Asp Asp Lys
1               5
```

(2) INFORMATION FOR SEQ ID NO:35:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

```
CAGTCAGCTA GCCGCCATGG ACTACAAGGA CGACGATGAC CAAGTTGACT GATGAAAAGG     60

TG                                                                   62
```

(2) INFORMATION FOR SEQ ID NO:36:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

```
CCAGAAGGGG TACTTTTCC                                                  19
```

(2) INFORMATION FOR SEQ ID NO:37:

(i) SEQUENCE CHARACTERISTICS:

(A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

CATTGTCCTG AGGCTGTGG                                                    19

(2) INFORMATION FOR SEQ ID NO:38:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

TATCCCAAAA GCCGACGGAT TTGCACTGTA CTTCCTTGGA GAGTGCAATA ATAGCCTGTG        60

TGTGTTCATA CCACCCGGGA TGAAGGAAGG CCAACCCCGG CTCATCCCTG CGGGGCCCAT       120

CACCCAGGGT ACCACCATCT CTGCCTACGT GGCCAAGTCT AGGAAGACGT TGTTGGTAGA       180

GGATATCCTT GGGGATGAGC GATTTCCTCG AGGTACTGGC CTGGAATCAG GAACCCGCAT       240

CCAGTCTGTT CTTTGCTTGC CCATTGTCAC TGCCATTGGA GACTTGATTG GCATCCTTGA       300

ACTGTACAGG CACTGGGACA AAGAGGCCTT CTGCCTCAGC CATCAGGAGG TTGCAACAGC       360

CAATCTTGCT TGGGCTTCCG TAGCAATACA CCAGGTGCAG GTGTGTAGAG GTCTCGCCAA       420

ACAGACCGAA CTGAATGACT TCCTACTCGA CGTATCAAAG ACATACTTTG ATAACAT          477

PHOSPHODIESTERASE 8A

BACKGROUND OF THE INVENTION

Phosphodiesterases (PDEs) hydrolyze 3', 5' cyclic nucleotides to their respective nucleoside 5' monophosphates. The cyclic nucleotides cAMP and cGMP are synthesized by adenylyl and guanylyl cyclases, respectively, and serve as second messengers in a number of cellular signalling pathways. The duration and strength of the second messenger signal is a function of the rate of synthesis and the rate of hydrolysis of the cyclic nucleotide.

Multiple families of PDEs have been identified. The nomenclature system includes first a number that indicates the PDE family. To date, seven families (PDE1–7) are known which are classified by: (i) primary structure; (ii) substrate preference; (iii) response to different modulators; (iv) sensitivity to specific inhibitors; and (v) modes of regulation [Loughney and Ferguson, in *Phosphodiesterase Inhibitors*, Schudt, et al. (Eds.), Academic Press: New York, N.Y. (1996) pp. 1–19]. The number indicating the family is followed by a capital letter, indicating a distinct gene, and the capital letter followed by a second number, indicating a specific splice variant or a specific transcript which utilizes a unique transcription initiation site.

The amino acid sequences of all mammalian PDEs identified to date include a highly conserved region of approximately 270 amino acids located in the carboxy terminal half of the protein [Charbonneau, et al., *Proc. Natl. Acad. Sci. (USA)* 83:9308–9312 (1986)]. The conserved domain includes the catalytic site for cAMP and/or cGMP hydrolysis and two putative zinc binding sites as well as family specific determinants [Beavo, *Physiol. Rev.* 75:725–748 (1995); Francis, et al., *J. Biol. Chem.* 269:22477–22480 (1994)]. The amino terminal regions of the various PDEs are highly variable and include other family specific determinants such as: (i) calmodulin binding sites (PDE1); (ii) non-catalytic cyclic GMP binding sites (PDE2, PDE5, PDE6); (iii) membrane targeting sites (PDE4); (iv) hydrophobic membrane association sites (PDE3); and (v) phosphorylation sites for either the calmodulin-dependent kinase II (PDE1), the cAMP-dependent kinase (PDE1, PDE3, PDE4), or the cGMP dependent kinase (PDE5) [Beavo, *Physiol. Rev.* 75:725–748 (1995); Manganiello, et al., Arch. Biochem. Acta 322:1–13 (1995); Conti, et al., *Physiol. Rev.* 75:723–748 (1995)].

Members of the PDE1 family are activated by calcium-calmodulin. Three genes have been identified; PDE1A and PDE1B preferentially hydrolyze cGMP while PDE1C has been shown to exhibit a high affinity for both cAMP and cGMP. The PDE2 family is characterized as being specifically stimulated by cGMP [Loughney and Ferguson, supra]. Only one gene has been identified, PDE2A, the enzyme product of which is specifically inhibited by erythro-9-(2-hydroxy-3-nonyl)adenine (EHNA). Enzymes in the PDE3 family are specifically inhibited by cGMP. Two genes are known, PDE3A and PDE3B, both having high affinity for both cAMP and cGMP, although the $V_{max}$ for cGMP hydrolysis is low enough that cGMP functions as a competitive inhibitor for cAMP hydrolysis. PDE3 enzymes are specifically inhibited by milrinone and enoximone [Loughney and Ferguson, supra]. The PDE4 family effects cAMP hydrolysis and includes four genes, PDE4A, PDE4B, PDE4C, and PDE4D, each having multiple splice variants. Members of this family are specifically inhibited by the anti-depressant drug rolipram. Members of PDE5 family bind cGMP at non-catalytic sites and preferentially hydrolyze cGMP. Only one gene, PDE5A, has been identified. The photoreceptor PDE6 enzymes specifically hydrolyze cGMP [Loughney and Ferguson, supra]. Genes include PDE6A and PDE6B (the protein products of which dimerize and bind two copies of a smaller γ inhibitory subunit to form rod PDE), in addition to PDE6C which associates with three smaller proteins to form cone PDE. The PDE7 family effects cAMP hydrolysis but, in contrast to the PDE4 family, is not inhibited by rolipram [Loughney and Ferguson, supra]. Only one gene, PDE7A, has been identified.

Given the importance of cAMP and cGMP in intracellular second messenger signalling, there thus exists an ongoing need in the art to identify addition PDE species. Identification of heretofore unknown families of PDEs, and genes and splice variants thereof, will provide additional pharmacological approaches to treating conditions in which cyclic nucleotide pathways are aberrant as well as conditions in which modulation of intracellular cAMP and/or cGMP levels in certain cell types is desirable.

SUMMARY OF THE INVENTION

In brief, the present invention provides polypeptides and underlying polynucleotides for a novel PDE family designated PDE8. The invention includes both naturally occurring and non-naturally occurring PDE8 polynucleotides and polypeptide products thereof. Naturally occurring PDE8 products include distinct gene and polypeptide species within the PDE8 family (i.e., PDE8A); these species include those which are expressed within cells of the same animal and well as corresponding species homologs expressed in cells of other animals. Within each PDE8 species, the invention further provides splice variants encoded by the same polynucleotide but which arise from distinct mRNA transcripts (i.e., PDE8A1 and PDE8A2). Non-naturally occurring PDE8 products include variants of the naturally occurring products such as analogs (i.e., wherein one or more amino acids are added, substituted, or deleted) and those PDE8 products which include covalent modifications (i.e., fusion proteins, glycolsylation variants, $Met^{-1}PDE8s$, $Met^{-2}-Lys^{-1}-PDE8s$, $Gly^{-1}PDE8s$ and the like). The PDE8 family is distinguished from previously known PDE families in exhibiting high affinity for hydrolysis of both cAMP and cGMP but relatively low sensitivity to enzyme inhibitors specific for other PDE families. In a preferred embodiment, the invention provides a polynucleotide comprising the sequence set forth in SEQ ID NO: 1. The invention also embraces polynucleotides encoding the amino acid sequence set out in SEQ ID NO: 2. A presently preferred polypeptide of the invention comprises the amino acid sequence set out in SEQ ID NO: 2. The invention provides two splice variant cDNAs which give rise to two polypeptides designated PDE8A1 and PDE8A2. PDE8A1 and PDE8A2 polypeptides, and the polynucleotides encoding the polypeptides, are discussed herein as representative of the PDE8 enzyme family embraced by the invention.

The present invention provides novel purified and isolated polynucleotides (e.g., DNA sequences and RNA transcripts, both sense and complementary antisense strands, including splice variants thereof) encoding the human PDE8s. DNA sequences of the invention include genomic and cDNA sequences as well as wholly or partially chemically synthesized DNA sequences. "Synthesized," as used herein and is understood in the art, refers to purely chemical, as opposed to enzymatic, methods for producing polynucleotides. "Wholly" synthesized DNA sequences are therefore produced entirely by chemical means, and "partially" synthesized DNAs embrace those wherein only portions of the resulting DNA were produced by chemical means. A preferred DNA sequence encoding a human PDE8 polypeptide is set out in SEQ ID NO: 1. Also preferred are polynucleotides encoding the PBE8 polypeptide of SEQ ID NO: 2 and the PDE8A1 and PDE8A2 splice variant polypeptides set out in SEQ ID NOs: 4 and 6, respectively. Preferred polynucleotides encoding PDE8A1 and PDE8A2 are set out in SEQ ID NOs: 3 and 5, respectively. The invention further embraces species, preferably mammalian, homologs of the human PDE8 DNA.

The invention also embraces DNA sequences encoding PDE8 species which hybridize under moderately stringent conditions to the non-coding strands, or complements, of the polynucleotides in SEQ ID NOs: 1, 3 and 5. DNA sequences encoding PDE8A polypeptides which would hybridize thereto but for the redundancy of the genetic code are contemplated by the invention. Exemplary moderate hybridization conditions are as follows: hybridization at 65° C. in 3×SSC, 0.1% sarkosyl, and 20 mM sodium phosphate, pH 6.8, and washing at 65° C. in 2×SSC with 0.1% SDS. It is understood in the art that conditions of equivalent stringency can be achieved through variation of temperature and buffer, or salt concentration as described Ausebel, et al. (Eds.), *Protocols in Molecular Biology,* John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), *Molecular Cloning: A Laboratory Manual,* Cold Spring Harbor Laboratory Press: Cold Spring Harbor, N.Y. (1989), pp. 9.47 to 9.51.

Autonomously replicating recombinant expression constructions such as plasmid and viral DNA vectors incorporating PDE8 sequences are also provided. Expression constructs wherein PDE8-encoding polynucleotides are operatively linked to an endogenous or exogenous expression control DNA sequence and a transcription terminator are also provided.

According to another aspect of the invention, host cells are provided, including procaryotic and eukaryotic cells, either stably or transiently transformed with DNA sequences of the invention in a manner which permits expression of PDE8 polypeptides of the invention. Host cells of the invention are a valuable source of immunogen for development of antibodies specifically immunoreactive with PDE8. Host cells of the invention are also conspicuously useful in methods for large scale production of PDE8 polypeptides wherein the cells are grown in a suitable culture medium and the desired polypeptide products are isolated from the cells or from the medium in which the cells are grown by, for example, immunoaffinity purification.

Knowledge of PDE8 DNA sequences allows for modification of cells to permit, or increase, expression of endogenous PDE8. Cells can be modified (e.g., by homologous recombination) to provide increased PDE8 expression by replacing, in whole or in part, the naturally occurring PDE8 promoter with all or part of a heterologous promoter so that the cells express PDE8 at higher levels. The heterologous promoter is inserted in such a manner that it is operatively-linked to PDE8 encoding sequences. See, for example, PCT International Publication No. WO 94/12650, PCT International Publication No. WO 92/20808, and PCT International Publication No. 91/09955. The invention also contemplates that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the PDE8 coding sequence, amplification of the marker DNA by standard selection methods results in co-amplification of the PDE8 coding sequences in the cells.

The DNA sequence information provided by the present invention also makes possible the development through, e.g. homologous recombination or "knock-out" strategies [Capecchi, *Science* 244:1288–1292 (1989)], of animals that fail to express functional PDE8 or that express a variant of PDE8. Such animals are useful as models for studying the in vivo activities of PDE8 and modulators of PDE8.

The invention also provides purified and isolated mammalian PDE8 polypeptides. Presently preferred PDE8A polypeptides are set out in SEQ ID NOs: 4 and 6. Most preferred is a PDE8 polypeptide comprising the amino acid sequence set out in SEQ ID NO: 2. PDE8 polypeptides of the invention may be isolated from natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention. PDE8 products of the invention may be full length polypeptides, biologically active fragments, or variants thereof which retain specific PDE8 biological activity. Variants may comprise PDE8 polypeptide analogs wherein one or more of the specified (i.e., naturally encoded) amino acids is deleted or replaced or wherein one or more non-specified amino acids are added: (1) without loss of one or more of the biological activities or immunological characteristics specific for PDE8; or (2) with specific disablement of a particular biological activity of PDE8.

Variant products of the invention include mature PDE8A products, i.e., PDE8 products wherein leader or signal sequences are removed, having additional amino terminal residues. PDE8 products having an additional methionine residue at position −1 (Met$^{-1}$-PDE8) are contemplated, as are PDE8 products having additional methionine and lysine residues at positions −2 and −1 (Met$^{-2}$-Lys$^{-1}$-PDE8). Variants of these types are particularly useful for recombinant protein production in bacterial cell types.

The invention also embraces PDE8 variants having additional amino acid residues which result from use of specific expression systems. For example, use of commercially available vectors that express a desired polypeptide such as a glutathione-S-transferase (GST) fusion product provide the desired polypeptide having an additional glycine residue at position −1 as a result of cleavage of the GST component from the desired polypeptide. Variants which result from expression in other vector systems are also contemplated.

The invention further embraces PDE8 products modified to include one or more water soluble polymer attachments. Particularly preferred are PDE8 products covalently modified with polyethylene glycol (PEG) subunits. Water soluble polymers may be bonded at specific positions, for example at the amino terminus of the PDE8 products, or randomly attached to one or more side chains of the polypeptide.

Also comprehended by the present invention are antibodies (e.g., monoclonal and polyclonal antibodies, single chain antibodies, chimeric antibodies, CDR-grafted antibodies and the like) and other binding proteins specific for PDE8 products or fragments thereof. Specific binding proteins can be developed using isolated or recombinant PDE8 products, PDE8 variants, or cells expressing such products. Binding proteins are useful for purifying PDE8 products and detection or quantification of PDE8 products in fluid and tissue samples using known immunological procedures. Binding proteins are also manifestly useful in modulating (i.e., blocking, inhibiting or stimulating) biological activities of PDE8, especially those activities involved in signal transduction. Anti-idiotypic antibodies specific for anti-PDE8 antibodies are also contemplated.

The scientific value of the information contributed through the disclosures of DNA and amino acid sequences of the present invention is manifest. As one series of examples, knowledge of the sequence of a cDNA for PDE8A makes possible through use of Southern hybridization or polymerase chain reaction (PCR) the identification of genomic DNA sequences encoding PDE8 and PDE8 expression control regulatory sequences such as promoters, operators, enhancers, repressors, and the like. DNA/DNA hybridization procedures carried out with DNA sequences of the invention under moderately to highly stringent conditions are likewise expected to allow the isolation of DNAs encoding allelic variants of PDE8A; allelic variants are known in the art to include structurally related proteins sharing one or more of the biochemical and/or immunological properties specific to PDE8A. Similarly, non-human species genes encoding proteins homologous to PDE8A can also be identified by Southern and/or PCR analysis. As an alternative, complementation studies can be useful for identifying other human PDE8 products as well as non-human proteins, and DNAs encoding the proteins, sharing one or more biological properties of PDE8A.

Polynucleotides of the invention are also useful in hybridization assays to detect the capacity of cells to express PDE8. Polynucleotides of the invention may also be the basis for diagnostic methods useful for identifying a genetic alteration(s) in a PDE8 locus that underlies a disease state or states.

Also made available by the invention are anti-sense polynucleotides which recognize and hybridize to polynucleotides encoding PDE8. Full length and fragment anti-sense polynucleotides are provided. Anti-sense polynucleotides are particularly relevant to regulating expression of PDE8 by those cells expressing PDE8 mRNA.

The DNA and amino acid sequence information provided by the present invention also makes possible the systematic analysis of the structure and function of PDE8s. DNA and amino acid sequence information for PDE8 also permits identification of molecules with which PDE8A will interact. Agents that modulate (i.e., increase, decrease, or block) PDE8 activity may be identified by incubating a putative modulator with PDE8 and determining the effect of the putative modulator on PDE8 phosphodiesterase activity. The selectivity of a compound that modulates the activity of the PDE8 can be evaluated by comparing its activity on the PDE8 to its activity on other PDE enzymes. Cell based methods, such as di-hybrid assays and split hybrid assays, as well as in vitro methods, including assays wherein a polypeptide or its binding partner are immobilized, and solution assays are contemplated by the invention.

Selective modulators may include, for example, antibodies and other proteins or peptides which specifically bind to the PDE8 or PDE8 nucleic acid, oligonucleotides which specifically bind to the PDE8 or PDE8 nucleic acid, and other non-peptide compounds (e.g., isolated or synthetic organic molecules) which specifically react with PDE8 or PDE8-encoding nucleic acid. Mutant forms of PDE8 which affect the enzymatic activity or cellular localization of the wild-type PDE8 are also contemplated by the invention. Presently preferred targets for the development of selective modulators include, for example: (1) regions of the PDE8 which contact other proteins and/or localize the PDE8 within a cell, (2) regions of the PDE8 which bind substrate, (3) allosteric cyclic nucleotide-binding site(s) of PDE8, (4) phosphorylation site(s) of PDE8 and (5) regions of the PDE8 which are involved in multimerization of PDE8 subunits. Modulators of PDE8 activity may be therapeutically useful in treatment of a wide range of diseases and physiological conditions in which PDE activity is known to be involved.

DETAILED DESCRIPTION OF THE INVENTION

The present invention is illustrated by the following examples which relate to the isolation of polynucleotides encoding PDE8 polypeptides as well as expression and characterization of the encoded polypeptides. Example 1 describes methods for searching expressed sequence tag (EST) databases in order to identify probes potentially useful for isolating DNAs of the invention. Example 2 relates to identification of PDE8A-encoding polynucleotides. Example 3 addresses sequence analysis of the isolated polynucleotides. Example 4 describes analysis of polypeptides encoded by the PDE8A polynucleotides. Example 5 addresses expression of recombinant PDE8A polypeptides. Example 6 relates to Northern analysis of PDE8A expression. Example 7 describes chromosome mapping of the gene encoding PDE8A.

EXAMPLE 1

Identification of an EST Related to a Human PDE

Using the sequences of known human, 3', 5' cyclic nucleotide phosphodiesterases, a search of the National Center for Biotechnology Information (NCBI) Expressed Sequence Tags (EST) database was undertaken in order to identify cDNA fragments that could potentially be useful for the identification of novel phosphodiesterase (PDE) genes. This database contains DNA sequences representing one or both ends of cDNAs collected from a variety of tissue sources. A single sequencing run is performed on one or both ends of the cDNA and the quality of the DNA sequence varies tremendously. At the time the PDE searches were performed, the EST sequence database contained more than 600,000 cDNA sequences from a variety of organisms.

The search for novel PDE sequences included three steps. First the BLASTN program available through NCBI was used to identify DNA sequences in the EST sequence database with homology to cDNA sequences encoding known human PDEs. The program compares a nucleotide query sequence against a nucleotide sequence database. The cDNA sequences of the fifteen known human PDEs were submitted and fifteen BLASTN searches were performed; the query PDE sequences included PDE1A3 [Loughney, et al.,*J. Biol. Chem.* 271:796–806 (1996)], PDE1B1 [Yu, et al., *Cell Signaling,* in press (1997)], PDE1C2 [Loughney, et al., *J. Biol. Chem.* 271:796–806 (1996)], PDE2A3 [Rosman, et al., *Gene* 191:89–95 (1997)], PDE3A [Meacci, et al., *Proc. Natl. Acad. Sci. (USA)* 89:3721–3725 (1992)], PDE3B [Miki et al., *Genomics* 36:476–485 (1996)], PDE4A5 [Bolger, et al., *Mol. Cell. Biol.* 13:6558–6571 (1993)], PDE4B2 [Bolger, et al., *Mol. Cell. Biol.* 13:6558–6571 (1993)], PDE4C [Bolger, et al., *Mol. Cell. Biol.* 13:6558–6571 (1993)], PDE4D1 and PDE4D3 [Bolger, et al., *Mol. Cell.*

*Biol.* 13:6558–6571 (1993)], PDE5A, PDE6A [Pittler, et al., *Genomics* 6:272–283 (1990)], PDE6B [Collins, et al., *Genomics* 13:698–704 (1992)],PDE6C [Piriev, et al., *Genomics* 28:429–435 (1995), and PDE7A1 [Michaeli, et al., *J. Biol. Chem.* 17:12925–12932 (1993)]. The BLASTN results were examined and EST sequences that were judged as corresponding to each of the fifteen known PDE cDNAs were identified and collected into a table. The PDE6A and PDE6B sequences used as queries were truncated at 3' end (removing a portion of the 3' untranslated region) due to the presence of repetitive elements in the 3' untranslated region of the cDNAs.

Secondly, the NCBI TBLASTN program was used to examine the homology between the protein sequence of the fifteen known human PDEs (as above) and the six different possible proteins encoded by each of the EST DNA sequences. In this search, the EST sequences are translated in six frames and the amino acid sequences generated are compared to the query PDE amino acid sequences. Sequences identified as homologous at the amino acid level were examined and any EST sequences positively identified as corresponding to a known PDE during the BLASTN search described above were discarded.

The third step of the search involved analyzing the sequences that were not known PDEs. These amino acid sequences were homologous to a known PDE but were not identified as one of the 15 known PDE genes during the BLASTN searches.

The BLAST searches identified an EST sequence (designated WO4835) from a human fetal lung cDNA library as encoding an amino acid sequence having homology to the catalytic region of PDE2A, PDE3A, PDE3B, PDE4A, PDE4B, PDE4C, PDE5A, rod alpha PDE6A, rod beta PDE6B, cone alpha PDE6C, and PDE7A. The database sequence for WO4835 is set out in SEQ ID NO: 7. Results from the database analysis as discussed below are exemplified using the PDE4D sequence.

WO4835 cDNA was obtained from American Type Culture Collection (Rockville, Md.) which maintains and makes publicly available deposits of ESTs identified and sequenced by I.M.A.G.E., Lawrence Livermore National Laboratory, Livermore, Calif.). The WO4835 DNA was sequenced upon receipt to confirm its identity and determined to be consistent with SEQ ID NO: 7.

The amino acid sequence encoded by the −1 reading frame of EST sequence WO4835 was recognized by all of the PDE query cDNA sequences except PDE1A, 1B and 1C. Using the TBLASTN results with PDE4D3 as an example, two regions of similarity were detected. The first region showed 15/37 exact matches or 40% identity (19/37 similar amino acids) and included the $HD(X)_2HXG(X)_{13}A$ (SEQ ID NO: 8) motif found in all of the query sequences. [Charboneau, *Mol. Pharmacol. Cell Regul.* 2:267–298 (1990)]. The second region showed 9/20 exact matches or 45% identity and included the YHNxxHA motif found in most of the query sequences. BLASTN analysis of the WO4835 sequence revealed that it was unique in that it was not identical to any other human DNA sequences in the Genbank database. The EST database entry for WO4835 identified the sequence as being similar to PIR:A48719, the bovine cGMP binding, cGMP hydrolyzing PDE5A1 sequence. Comparison of the protein sequence of WO4835 frame—1 to the bovine PDE5A1 sequence revealed 58/153 matches for an overall identify of 38%. Within this region were small regions of greater homology; one region showed a 12/14 identical amino acids. Given the unique nature of the WO4835 sequence, its relatively low homology to bovine PDE5A1, and the presence of the amino acid motifs found in most other known human PDE amino acid sequences, WO4835 represents a novel human PDE cDNA.

EXAMPLE 2

Isolation of Putative PDE cDNA

WO4835 cDNA insert was digested from the pT7T3D vector into two fragments with the restriction enzymes EcoRI and HindIII and the two fragments were purified using two sequential low melting agarose gels. Both fragments were used as probes to screen cDNA libraries derived from human heart (Stratagene, La Jolla, Calif.), and human fetal brain (Stratagene) using procedures routinely practiced in the art. Approximately $5 \times 10^5$ phage from each library were screened. Hybridization was carried out overnight in buffer containing 3×SSC, 0.1% Sarkosyl, 20 mM sodium phosphate, pH 6.8, 10×Denhardt's solution, and 50 µg/ml salmon sperm DNA at 65° C. The filters were washed at 65° C. in buffer containing 2×SSC and 0.1% SDS prior to autoradiography.

Nine clones from the fetal brain cDNA library and two from the heart cDNA library hybridized to the WO4835 probe. Partial sequencing and mapping led to the selection of one clone from the fetal brain library designated FB66a for further characterization.

A second screening of approximately $7.5 \times 10^5$ phage from the fetal brain cDNA library under conditions used in the first screening using the 1.3 kb EcoRI/HindIII fragment from the 5' portion of WO4835 yielded nineteen additional cDNA clones. Six of these cDNAs also hybridized to a HindIII/KpnI fragment of WO4835 which includes a 256 nucleotide region at the 5' end of WO4835. Partial sequencing and mapping of five of the clones led to the selection of a second clone designated FB85c-2 for further analysis.

EXAMPLE 3

DNA Sequence Analysis of FB66a and FB85c-2

The DNA sequence of FB66a was determined for both strands using DNA oligonucleotide primers set out below in SEQ ID NOs: 9 to 31 and a Perkin Elmer Applied Biosystems Division 373A DNA Sequencer according to the maunfacturer's suggested protocol. The amount of PCR product used as template was calculated based on the size of the PCR product and was sequenced using ABI PRISM Dye Terminator Cycle Sequencing Ready Reaction Kit with ApliTaq DNA Polymerase, FS (Perkin Elmer, Foster City, Calif.) and asymmetric PCR. The reaction product was purified on a AGCT spin column (Advanced Genetic Technologies Corp., Gaithersburg, Md.) and dried. Loading buffer was added to each purified sample and the mixture heated at 90° C. for two minutes. The solution was transferred to ice until being loaded onto a 4% polyacrylamide gel. Data was automatically collected once the Data Collection program was initiated and was automatically analyzed and read by the Sequence Analysis program. All editing was performed manually and the resulting sequences were aligned where the consensus sequence was determined.

| M13Rev.1 | GGAAACAGCTATGACCATG | SEQ ID NO: 9 |
|---|---|---|
| W48A2 | ACTCTCCAAGGAAATACAG | SEQ ID NO: 10 |

| | | |
|---|---|---|
| W48A9 | CTGTCTCTGCACTAACAC | SEQ ID NO: 11 |
| W48A4 | TTGGCAAGGCCTCTGCAT | SEQ ID NO: 12 |
| W48S1 | CCTCTATGAACTGAGCAG | SEQ ID NO: 13 |
| W48A1 | GAAGGCACTGCCACTGAT | SEQ ID NO: 14 |
| W48S6 | TCGAGCTGTATCGGCACT | SEQ ID NO: 15 |
| W48A5 | AGCGTGTGATTGTTCTGAA | SEQ ID NO: 16 |
| W48S7 | TGCTGGCCAAGTAGCAAG | SEQ ID NO: 17 |
| W48A6 | AAGGTCACAGGCAGTCAT | SEQ ID NO: 18 |
| W48S2 | GAAGAGTGGCAAGGTCTC | SEQ ID NO: 19 |
| W48S3 | TCATGACCTGGACCACCAG | SEQ ID NO: 20 |
| W48A8 | CCTTCTTGAAGAGGTTTGC | SEQ ID NO: 21 |
| W48S4 | ATGACTGCCTGTGACCTT | SEQ ID NO: 22 |
| W48S5 | CTGCTATACAACCCTTACC | SEQ ID NO: 23 |
| W48S8 | GCTAATATTGCTGAGGCC | SEQ ID NO: 24 |
| W48A7 | TAAGTGAGAGGTGACTGC | SEQ ID NO: 25 |
| W48S9 | CCTAAAGGGCTGAGATCA | SEQ ID NO: 26 |
| W48S10 | CGCAGTCACCTCTCACTT | SEQ ID NO: 27 |
| M13 | TGTAAAACGACGGCCAGT | SEQ ID NO: 28 |
| W48A11 | ACAAAACGCCTATGGTGG | SEQ ID NO: 29 |
| W48A10 | TTGATCTCAGCCCTTTAGC | SEQ ID NO: 30 |
| W48S11 | TCATGTGGCAGGAAACTG | SEQ ID NO: 31 |

The FB66a cDNA, set out in SEQ ID NO: 3, is 4389 nucleotides in length and, from nucleotide 3 to nucleotide 2411, encodes a protein of 803 amino acids with a predicted molecular weight of approximately 90,775 Da. The deduced amino acid sequence for FB66a is set out in SEQ ID NO: 4. The first methionine is encoded at nucleotide 45; the absence of an upstream in frame stop codon makes it unclear whether this residue is an internal methionine or the beginning of the open reading frame.

The DNA sequence of FB85c-2 (SEQ ID NO: 5) was similarly determined using primers M13Rev.1, W48A2, W48A9, W48A4, W48S1, W48A1, W48S6, W48A5, W48A6, W48S2, W48S3, W48S4, W48S5, W48S7, W48A8, and M13. FB85c-2 appeared to include two distinct DNA inserts, only one of which was homologous to WO4835. The region homologous to WO4835 was approximately 2.8 kb in length. The precise sequence at the 5' end of the insert could not be determined and thus a few hundred bases of sequence in what may be a 5'-untranslated region are not included in the 2573 nucleotide sequence set out in SEQ ID NO: 5. Nucleotide 67 to nucleotide 2406 encodes a protein having 779 amino acid protein (SEQ ID NO: 6) having a predicted molecular weight of 88,353 Da. An in frame upstream stop codon makes it likely that the methionine encoded at nucleotide position 67 is the initiation methionine.

The proteins encoded by FB66a and FB85c-2 have different amino terminal sequences which may be due to alternative splicing. The DNA sequences diverge from each other 5' of nucleotide 112 in FB66a and nucleotide 104 in FB85c-2. Thus, FB85c-2 has 13 amino acids at the amino terminus that are not found in the FB66a protein. The FB66a protein includes 23 unique amino terminal residues if the initiating methionine at presumed to be encoded at nucleotide 35; the protein includes more than 37 unique amino terminal residues if the open reading frame in the FB66a clone is incomplete.

BLASTN analysis, wherein a query nucleotide sequence is compared against a nucleotide sequence database, of the FB66a sequence revealed no identity with sequences in Genbank, NCBI STS, NCBI HTGS, or NCBI GSS databases. However, two identical sequences were identified in the NCBI EST database.

One sequence was the WO4835 EST which was used to identify the cDNA clone. The second, AA307865 (SEQ ID NO: 32), derived from a colon cancer cell line KM12C (HCC) showed sequence identity with the 3' untranslated region of the FB66a and FB85c-2 clones. During the search in which AA307865 was identified, additional EST DNAs were identified presumably encoding putative mouse (EST AA386789, SEQ ID NO: 38) and rat (EST H32734, SEQ ID NO: 33) homologs to the human proteins encoded by FB66a and FB85c-2. The mouse sequence was 86% identical to the human sequences and the rat sequence was 81%.

EXAMPLE 4

Analysis FB85c-2 and FB66a Protein

The PDEs encoded by clones FB85c-2 and FB66a were designated PDE8A1 and PDE8A2, respectively. Both PDE8A proteins, having complete amino acid sequence identity beyond the point of divergence discussed above, are most similar to human PDE2A, PDE5A, PDE6A, PDE6B, and PDE6C. Tables 1 and 2 show percent amino acid identity between PDE8A and PDE2A, PDE5A and PDE6A.

PDE8A1 and PDE8A2 share homology with other PDEs over the catalytic region (amino acids 492 through 748 in PDE8A1) and with the putative cGMP binding domain conserved in the amino terminal region of the PDE2A, PDE5A, PDE6A, PDE6B, AND PDE6C. The potential cGMP binding domain of PDE8A extends from amino acids 75 to amino acid 445 in the PDE8A1 polypeptide. Within the cGMP binding domains of PDE2A, PDE5A, PDE6A, PDE6B, and PDE6C, there are two internal repeats designated "a" and "b," and each repeat contains a series of conserved amino acids [McAllister-Lucas, et al., *J. Biol. Chem.* 268:22863–22873 (1993)]. In the corresponding "b" repeat region of PDE8A, all of the conserved amino acids are found; in the corresponding "a" repeat region, only some of the conserved residues were detected. An aspartate residue, shown to be essential for the cGMP binding by bovine PDE5A [McAllister-Lucas, et al., *J. Biol. Chem.* 270:1–9 (1995)] is not present in the "a" repeat region of PDE8A. It is therefore uncertain whether this region in PDE8A functions to bind cGMP.

TABLE 1

PDE8A Identity in the Entire Protein

| PDE | 2A | 5A | 6A | 8A |
|---|---|---|---|---|
| 2A | 100 | 19 | 16 | 28 |
| 5A | | 100 | 23 | 28 |
| 6A | | | 100 | 21 |
| 8A | | | | 100 |

TABLE 2

PDE8A Identity in the Catalytic Domain

| PDE | 2A | 5A | 6A | 8A |
|---|---|---|---|---|
| 2A | 100 | 38 | 33 | 41 |
| 5A |  | 100 | 42 | 46 |
| 6A |  |  | 100 | 37 |
| 8A |  |  |  | 100 |

EXAMPLE 5

Expression of Recombinant PDE8A

An expression construct for PDE8A was generated that included DNA sequences 3' from the point of divergence of PDE8A1 and PDE8A2 through the stop codon. The expression construction included DNA encoding an eight amino acid epitope tag. The so-called "FLAG tag," comprising the peptide sequence set out in SEQ ID NO: 34, was added to the amino terminus in order that the protein could be identified by Western blotting techniques using an anti-FLAG M2 antibody (Eastman Kodak, Rochester, N.Y.) which specifically recognized the peptide of SEQ ID NO: 34.

SEQ ID NO: 34 Asp-Tyr-Lys-Asp-Asp-Asp-Asp-Lys
Sequences encoding an initiating methionine at the proteins amino terminus was also added.

As a first step in constructing the expression plasmid, PCR was performed using FB66a DNA as a template using primers set out in SEQ ID NOs: 35 (below) and W48A2 (SEQ ID NO: 10, p. 14) in a reaction mixture containing 2 µl each primer (stock 100 µg/ml), 2 µl 10×PCR buffer II (Perkin Elmer), 2 µl 10× stock of each nucleotide (stock 2 mM), 1.2 µl MgCl$_2$ (stock 25 mM), 0.09 µl 5 Units/µl taq polymerase (Perkin Elmer), FB66a DNA and water to bring the reaction mixture to 20 µl. In the 5' primer (SEQ ID NO: 35), an NcoI site is in bold and the FLAG tag encoding region is underlined.

SEQ ID NO: 35
CAGTCAGCTAGCCGCCATGG<u>ACTACAAGGAC-
GACGATGACAAG</u>TTGACTGATGAAAAGGTG

PCR was carried out in a Perkin Elmer DNA Thermal Cycler under the following conditions: 94° C. for 4 minutes followed by 30 cycles of 94° C. for one minute, 50° C. for one minute, and 72° C. for two minutes.

The resulting PCR product was digested with NcoI and KpnI, gel purified, and subcloned into Bluescript SKII$^+$ vector previously digested with the same enzymes. The Bluescript vector had previously been modified to include a SacI/NcoI alcohol dehydrogenase 2 (ADH2) promoter fragment removed from a YEpC-PADH2d vector [Price, et al., Meth. Enzymol. 185:308–315 (1990)]. The resulting plasmid was designated W48pcr1.

A KpnI/SstI fragment containing the 3' portion of the open reading frame was isolated from a FB66a cDNA and inserted into W48pcr1 previously digested with KpnI and EcoRV. The resulting plasmid was designated W485.1.

A SacI/KpnI fragment containing the ADH2 promoter and the 5' portion of the PDE8A gene was isolated from W49pcr1. A KpnI/SalI fragment containing the 3' region of PDE8A was isolated from W485.1. The two fragments were ligated into the yeast expression vector YEpC-PADH2d that had been previously digested with SacI and SalI. The resulting plasmid was designated W48-2ADH2 and was deposited on Oct. 2, 1997 under the terms of the Budapest Treaty with the American Type Culture Collection (A.T.C.C.), 10801 University Blvd., Manassas, Va. 20110-2209. The bacterial strain bearing plasmid W48-2ADH2 was assigned accession number ATCC 98552. The DNA sequences generated by PCR and the DNA sequences at the PDE8/vector junctions were determined to insure proper plasmid construction. Upon confirmation of the sequence, the plasmid was transformed into a yeast strain BJ2-54 lacking endogenous PDE activity (ura3-52;trp1;leu2;cir°;gal2; pep4-3,prb1-1122,prc1-402;ΔPDE1::URA3;HIS3;ΔPDE2::TRP1).

The host cells were grown overnight in SC-leu selective media including 2% glucose, diluted to 1–2×10$^5$ cells/ml and subsequently grown to a density of 10$^7$ cells/ml in the same media. The presence of the expression plasmid appeared to increase the doubling time for cell growth two- to three-fold even under non-inducing conditions. The cells were collected by centrifugation, washed with YEP media including 3% glycerol, resuspended in YEP/3% glycerol at a density of 10$^7$ cells/ml, and grown for 24 hours prior to harvest. Cells were frozen until use.

Frozen cell pellets (0.06 ml) were thawed and suspended in 0.2 ml lysis buffer containing 100 mM MOPS, pH 8.0, 200 mM NaCl, 2 µM ZnSO$_2$, 2 mM dithiothreitol, and 10 µg/ml each protease inhibitors pepstatin, leupeptin, and aprotinin. Approximately 0.2 ml of 0.5 mm glass beads were added to the cells which were then lysed with four 30-second cycles of vortexing. The lysate was aspirated and the beads were washed twice with 0.3 ml lysis buffer. The lysate was combined with the washes to generate the yeast extract. In some experiments the lysate was fractionated by centrifugation at 105,000×g for thirty minutes.

Western analysis was carried out on yeast extract containing the recombinant protein as follows. Proteins were first separated on SDS-PAGE and transferred to Immobilon-P (Millipore) using standard methods. The protein blots were blocked using 5% non-fat dry milk in 20 mM Tris-HCl, pH 7.4, 150 mM NaCl, 0.05% Tween-20 (TBST buffer plus milk) for one hour at room temperature. The blots were incubated with anti-FLAG M2 antibody (discussed above) at a concentration of 1 µg/ml in TBST buffer plus milk for one hour, after which the blots were washed four times with TBST buffer. The blots were then incubated for one hour with blotting grade affinity purified goat anti-mouse IgG antibody conjugated to horse radish peroxidase (HRP) (BioRad). The goat IgG was previously diluted 1:10,000 in TBST buffer plus milk. The blots were washed four times with TBST and treated, according to the manufacturer's suggested protocol, with the Renaissance® system (New England Nuclear Life Sciences Products) for enhanced chemiluminescence prior to autoradiography. The majority of the protein detected by the antibody was the size expected for the recombinant protein.

PDE activity was assayed by detection of $^{32}$P-phosphate released from $^{32}$P-cAMP or $^{32}$P-cGMP as described previously [Loughney et al., J. Biol. Chem. 271:796–806 (1996)]. The yeast extract was diluted in 0.5× lysis buffer also containing 0.5 mg/ml bovine serum albumin. Twenty µl of the yeast extract, or diluted yeast extract, was assayed in a 100 µl reaction volume which included an additional 50 mM Tris-HCl (pH 8.0), 5 mM MgCl$_2$ 1 µM Zn SO$_2$, and 0.1 mg/ml bovine serum albumin. Protein concentration was assayed by the method of Bradford.

PDE8A was observed to hydrolyze both cAMP and cGMP. In unfractionated lysates, the specific activity for cAMP was 3.9 nmol/min/mg and for cGMP was 7.6 nmol/ min/mg. Fractionation revealed that 20–40% of the total activity was associated with the high speed supernatant fraction. Kinetic analysis of the activity with cAMP as substrate suggested the presence of both low and high $K_m$ forms of the enzyme in a 1:1 activity ratio. The estimated $K_m$ values were 0.2 μM and 350 μM. Analysis of the high speed pellet suggested that the same species were present but in a high $K_m$:low $K_m$ activity ratio of 1:4. Kinetic analysis with cGMP as substrate also suggested the presence of low and high forms of the enzyme. In these analyses, $K_m$ values were estimated to be 3 μM and 300 μM.

The $IC_{50}$ values for inhibition of PDE8A activity were determined using a set of isozyme-selective PDE inhibitors and the non-selective inhibitor isomethyl butyl xanthine (IBMX). Since these assays were performed at a cAMP concentration of 60 nM, the $IC_{50}$ values reflect inhibition of the low $K_m$ form only. The results are set out in Table 3 with values shown in micromolar units.

TABLE 3

PDE8 Inhibition with Isozyme-specific PDE Inhibitors

| Compound | Target PDE Family | $IC_{50}$ for Target Family | $IC_{50}$ for PDE8 | Fold Difference |
| --- | --- | --- | --- | --- |
| IC224 | PDE1 | 0.08–0.008 | 2.7 | 38–338 |
| EHNA | PDE2 | 2 | 65 | 31 |
| Cilostamide | PDE3 | 0.02 | 12 | 750 |
| IC197 | PDE4 | 0.02 | 14 | 714 |
| DMPPO | PDE5 | 0.016 | 1.1 | 66 |
| IBMX | Non-selective | 1–40 | 4.6 | 0.12–4.6 |

The $IC_{50}$ values for each of the selective inhibitors were at least 30 times higher against PDE8 than against their target isozymes which suggests that the inhibitory profile of PDE8 is distinct from that of PDEs 1–5. The hydrolysis of cAMP and cGMP clearly distinguishes the enzymatic activity of PDE8A from that of PDE6 and PDE7A. The $IC_{50}$ of the non-selective inhibitor IBMX for PDE8 was in the range observed for known human PDEs suggesting that the catalytic site of PDE8 resembles those of other human and mammalian PDEs and is distinct from lower eukaryotic forms that are insensitive to IBMX.

EXAMPLE 6

Northern Analysis of PDE8A Expression

Northern analysis of PDE8A expression was carried out using a human multiple tissue blot (Clontech, Palo Alto, Calif.). The 327 base probe was extended from nucleotide 1767 to nucleotide 2293 in SEQ ID NO: 3. Riboprobe preparation and hybridization conditions were as previously described [Loughney, et al. supra].

Results showed a 9.5 kb mRNA in all tissues examined but band intensity varied. The signal was strongest in heart, brain, and kidney; the signal was weaker in liver, placenta, pancreas, and skeletal muscle. The signal was weakest in lung.

EXAMPLE 7

Chromosome Mapping of Human PDE8A

Yeast artificial chromosomes (YACs) containing the human PDE8A gene were isolated from a panel of human YACs purchased from Research Genetics and screened by PCR as follows.

The YAC super-pools were screened with two nested pairs of primers. In the first screening reaction, sense primer W48S8 (SEQ ID No: 36) was paired with the anti-sense primer W48A10 (SEQ ID NO: 37). PCR was carried out with 10 mM Tris-HCl, pH 8.3, 50 mM KCl, 2 mM $MgSO_4$, 0.2 mM of each dNTP, 10 μg/ml of each primer, 0.5 units of Taq polymerase (Perkin-Elmer) and 1.5 μl of YAC pool DNA as template. Reactions were carried out for 30 cycles, each cycle consisting of one minute at 94° C., two minutes at 60° C., and four minutes at 72° C. After the first round of amplification, the reaction products were reamplified with the internal pair of primers W48S12 (SEQ ID NO: 36) and W48A12 (SEQ ID NO: 37).

```
W48S12                              SEQ ID NO: 36
        CCAGAAGGGGTACTTTTCC

W48A12                              SEQ ID NO: 37
        CATTGTCCTGAGGCTGTGG
```

The reactions were carried out as described above except that the template was 1 μl of a 1:10 dilution (in water) of the first round reaction. Super-pools yielding the correct size PCR product were identified and the corresponding sub-pools were screened with the same nested pairs of primers under the same conditions to identify unique addresses for YACs containing PDE8A.

Yeast strains harboring the relevant YACs were purchased from Research Genetics. In order to verify the presence of the PDE8A gene in the various YACs, DNA was prepared from each strain and analyzed by PCR with primers W48S8 and W48A10. DNA was prepared from each strain according to a method previously described [Hoffman and Winston, Gene 57:267–272 (1987)] but modified as follows. Strains were grown overnight at 30° C. in YEP media containing glucose. Ten ml of culture was pelleted by centrifugation and resuspended in 200 μl of aqueous buffer containing 10 mM Tris-HCl, pH 8.0, 100 mM NaCl, 1 mM $Na_2EDTA$, 1% SDS, and 2% Triton-X100. The cells were lysed by vortexing in the presence of 200 μl of phenol/chloroform (1:1 mixture) and 100 μl of glass beads (425–600 μm). Following lysis, 200 μl of TE Buffer (10 mM Tris, pH 8.0, 1 mM $Na_2EDTA$) was added and the sample was centrifuged to separate the phases. The organic phase was extracted again with 200 μl of aqueous buffer. The pooled aqueous phase was treated with 100 units of bovine pancreatic RNase (Boehringer Mannheim) for 1 hour at 37° C. and the sample was extracted with phenol/chloroform, re-extracted with chloroform, and ethanol precipitated according to established methods. The resultant pellet was resuspended in 50 μl TE Buffer. PCR was carried out as described above except that the reaction volume was 25 μl and the template consisted of 1 μl of the relevant yeast DNA preparation.

Three human YACs containing the PDE8 gene were identified with addresses 805B6, 919H10 and 920A3 (as per the CEPH designation). According to information in the Center for Genome Research database (Whitehead), the three YACs overlap one another and are part of a singly-linked contig (WC6.16) on human chromosome 6. Two sequence tagged sites within this contig (D6S305 and D6S411) have been placed on the chromosomes 6 genetic map at a position 167 cM from the end of 6p in work at the Center for Genome Research; D6S305 has been mapped to a position 173 cM from the end of 6p in work at CEPH-Genethon. Three other YACs within the WC6.16 contig (932F1, 956B1 and 947D5) have been mapped by florescence in situ hybridization at CEPH-Genethon. The hybridization signals fall between 0.94- and 0.99 fractional length units from the end of 6p. According to the CEPH integrated summary map [Chumakov et al., Nature 377

(Supp):175–297 (1995)], this region corresponds to the cytogenetic region 6q26–27.

Heritable defects that have been associated with this region of the human genome include retinal cone degeneration (OMIM database), Insulin-dependent diabetes mellitus [Davies et al. *Nature* 371:130–136 (1994); Luo et al. *Am. J. Hum. Genet.* 57:911–919 (1995)] and juvenile onset parkinsonism [Matsumine et al. *Am. J. Hum. Genet.* 60:588–596 (1997)]. In addition, loss of heterozygosity (LOH) is frequently observed in this region in a variety of different cancer cells, including Burkitt's lymphoma [Parsa et al. *Genes, Chromosomes & Cancer* 9:13–18 (1994)], astrocytoma [Liang et al. *Neurology* 44:533–536 (1994)], gastric carcinoma [Queimado et al. *Genes, Chromosomes & Cancer* 14:28–34 (1995)], parathyroid adenoma [Tahara et al. *Cancer Res.* 56:599–605 (1996)] and ovarian carcinoma [Cooke et al. *Genes, Chromosomes & Cancer* 15:223–233 (1996); Saito et al. *Cancer Res.* 56:5586–5589 (1996)]. LOH has been suggested to indicate the presence of a tumor suppressor gene in the affected region [Weinberg, *Science* 254:1138–1146 (1991)]. Due to its widespread expression, it is possible that mutation of the PDE8 gene may be involved in all or some of these genetic abnormalities.

Numerous modifications and variations in the invention as set forth in the above illustrative examples are expected to occur to those skilled in the art. Consequently only such limitations as appear in the appended claims should be placed on the invention.

What is claimed is:

1. A purified and isolated polynucleotide encoding a polypeptide selected from the group consisting of a phosphodiesterase 8 (PDE8) polypeptide, the polypeptide set forth in SEQ ID NO:2, the polypeptide set forth in SEQ ID NO:4, and the polypeptide set forth in SEQ ID NO:6.

2. The polynucleotide according to claim 1 comprising the sequence set forth in SEQ ID NO: 1.

3. The polynucleotide according to claim 1 comprising the in SEQ ID NO: 3.

4. The polynucleotide according to claim 1 comprising the sequence set forth in SEQ ID NO: 5.

5. A polynucleotide encoding a human phosphodiesterase 8 (PDE8) polypeptide selected from the group consisting of:
    a) the polynucleotide according to any one of claims 2, 3, and 4; and
    b) a DNA which hybridizes under moderately stringent conditions to the polynucleotide of (a), said moderately stringent conditions comprising a final wash at 65° C. in 2×SSC and 0.1% SDS.

6. A polynucleotide encoding a human phosphodiesterase 8 (PDE8) polypeptide selected from the group consisting of:
    a) the polynucleotide according to claim 1; and
    b) a DNA which hybridizes under moderately stringent conditions to the polynucleotide of (a), said moderately stringent conditions comprising a final wash at 65° C. in 2×SSC and 0.1% SDS.

7. The polynucleotide of claim 1 which is a DNA molecule.

8. The DNA of claim 7 which is a cDNA molecule.

9. The DNA of claim 7 which is a genomic DNA molecule.

10. The DNA of claim 7 which is a wholly or partially chemically synthesized DNA molecule.

11. An anti-sense polynucleotide which specifically hybridizes with the complement of the polynucleotide of claim 1.

12. A expression construct comprising the polynucleotide according to claim 1.

13. A host cell transformed or transfected with the polynucleotide according to claim 12.

14. A method for producing a phosphodiesterase 8 (PDE8) polypeptide comprising the steps of:
    a) growing the host cell according to claim 13 under conditions appropriate for expression of the PDE8 polypeptide and
    b) isolating the PDE8 polypeptide from the host cell or the medium of its growth.

* * * * *

UNITED STATES PATENT AND TRADEMARK OFFICE
CERTIFICATE OF CORRECTION

PATENT NO. : 5,932,465
DATED : August 3, 1999
INVENTOR(S) : Kate Loughney

It is certified that error appears in the above-identified patent and that said Letters Patent is hereby corrected as shown below:

On the title page,

Item [56] Chumakov et al.: Please delete "cotig", and insert - -contig- -.

Signed and Sealed this

Fifth Day of December, 2000

Attest:

Q. TODD DICKINSON

*Attesting Officer*       *Director of Patents and Trademarks*